US011540791B2

(12) United States Patent
Goederer et al.

(10) Patent No.: US 11,540,791 B2
(45) Date of Patent: Jan. 3, 2023

(54) METHOD FOR GENERATING AN X-RAY IMAGE DATASET

(71) Applicant: Siemens Healthcare GmbH, Erlangen (DE)

(72) Inventors: Edgar Goederer, Forchheim (DE); Martin Hupfer, Erlangen (DE); Bjoern Kreisler, Hausen (DE); Martin Petersilka, Adelsdorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 35 days.

(21) Appl. No.: 17/116,073

(22) Filed: Dec. 9, 2020

(65) Prior Publication Data

US 2021/0186439 A1    Jun. 24, 2021

(30) Foreign Application Priority Data

Dec. 18, 2019   (EP) .................................... 19217564

(51) Int. Cl.
*A61B 6/00* (2006.01)
*A61B 6/03* (2006.01)

(52) U.S. Cl.
CPC ............ *A61B 6/4241* (2013.01); *A61B 6/032* (2013.01); *A61B 6/4233* (2013.01); *A61B 6/5205* (2013.01)

(58) Field of Classification Search
CPC ..... A61B 6/032; A61B 6/4233; A61B 6/4241; A61B 6/5205
See application file for complete search history.

(56) References Cited

U.S. PATENT DOCUMENTS 4,476,386 A * 10/1984 Reid .................. G01N 23/2252
250/307
8,772,730 B2    7/2014 Han et al.
(Continued)

FOREIGN PATENT DOCUMENTS

DE    102011077859 B4    1/2014
DE    102012224209 A1    7/2014

OTHER PUBLICATIONS

Hsieh, Scott S. et. al., "Digital count summing vs analog charge summing for photon counting detectors: A performance simulation study" in: Med. Phys. 45 (9), pp. 4085-4093, Sep. 2018.
(Continued)

*Primary Examiner* — Blake C Riddick
(74) *Attorney, Agent, or Firm* — Harness, Dickey & Pierce, P.L.C.

(57) ABSTRACT

A method is for generating an X-ray image dataset via an X-ray detector having a converter element and a multiplicity of pixel elements. In an embodiment, the method includes first counting of at least one quantity of count signals dependent upon the incident X-ray radiation in each pixel element of the multiplicity of pixel elements; second counting of at least one quantity of coincidence count signals in each pixel element of the subset of pixel elements with at least one further pixel element of the multiplicity of pixel elements; and generating an X-ray image dataset based upon the at least one quantity of count signals counted in each pixel element of the multiplicity of pixel elements and upon the at least one quantity of coincidence count signals counted in each pixel element of the subset of pixel elements.

26 Claims, 8 Drawing Sheets

(56) References Cited

U.S. PATENT DOCUMENTS

| | | | |
|---|---|---|---|
| 2007/0206721 A1* | 9/2007 | Tkaczyk | H04N 5/379 378/19 |
| 2011/0210235 A1* | 9/2011 | Dierickx | G01T 1/17 250/214 R |
| 2012/0326049 A1 | 12/2012 | Hannemann et al. | |
| 2014/0175299 A1 | 6/2014 | Spahn | |
| 2016/0245934 A1* | 8/2016 | Shahar | G01T 7/005 |
| 2017/0016998 A1* | 1/2017 | Shahar | G01T 1/247 |
| 2017/0269240 A1* | 9/2017 | Shahar | G01T 1/249 |
| 2018/0180748 A1* | 6/2018 | Shahar | G01T 1/246 |
| 2018/0259657 A1* | 9/2018 | Fu | G01T 1/366 |
| 2019/0285469 A1 | 9/2019 | Cherlin et al. | |
| 2020/0342637 A1* | 10/2020 | Zhang | G06T 7/0012 |

OTHER PUBLICATIONS

Hsieh, S., "Coincidence counters for charge sharing compensation in spectroscopic photon counting detectors", IEEE Transactions on Medical Imaging, doi: 10.1109/TMI.2019.2933986.

\* cited by examiner

FIG 5
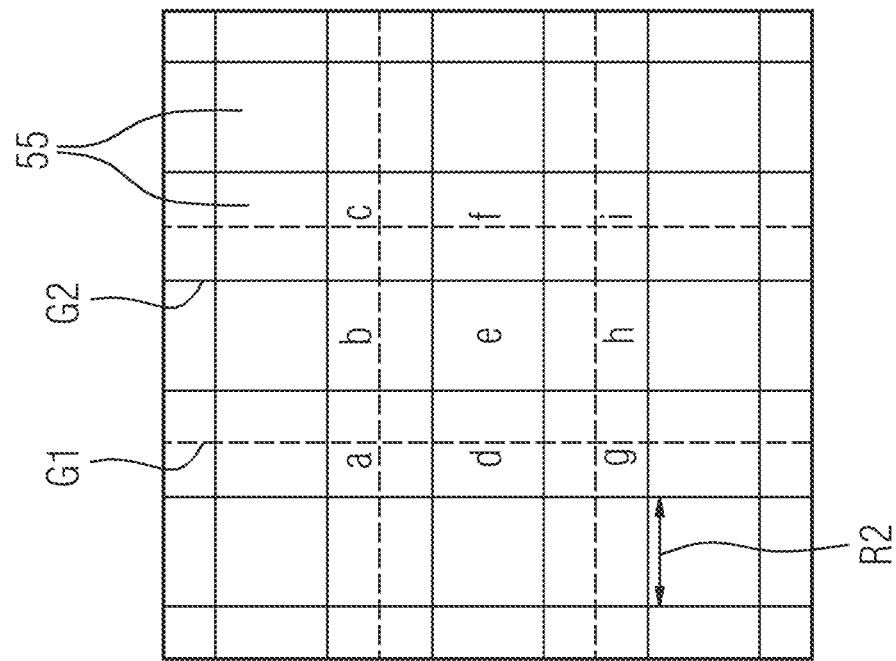
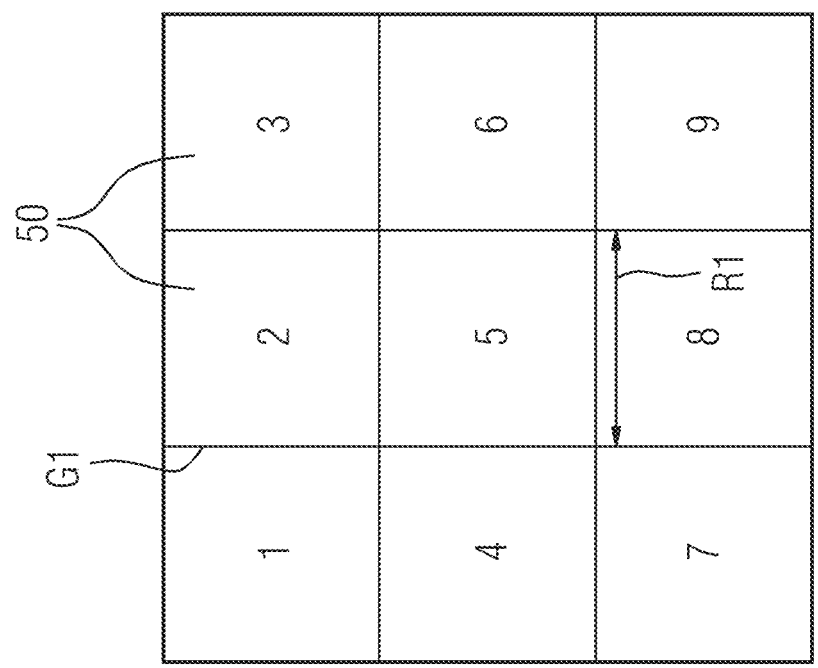

METHOD FOR GENERATING AN X-RAY IMAGE DATASET

PRIORITY STATEMENT

The present application hereby claims priority under 35 U.S.C. § 119 to European patent application number EP19217564.4 filed Dec. 18, 2019, the entire contents of which are hereby incorporated herein by reference.

FIELD

Example embodiments of the application generally relate to a method for generating an X-ray image dataset, an X-ray detector system having a photon-counting X-ray detector and a medical imaging device having an X-ray detector system with a photon-counting X-ray detector.

BACKGROUND

Photon-counting X-ray detectors are used in many imaging applications. These X-ray detectors are used, for example, in computed tomography systems in medical imaging in order to generate a tomographic X-ray image of an examination region of a patient.

The use of photon-counting detectors in X-ray imaging offers a series of advantages over energy-integrating detectors. They enable a high level of spatial resolution and an intrinsically energy-resolving scan. The image quality of present-day photon-counting X-ray detectors, however, is limited by the finite extent of the charge clouds generated (and by the generation of characteristic X-ray radiation) in the detector material. This has the result that the entire energy of the X-ray photon is not always deposited in the pixel concerned, but a part of the energy is registered in one or more adjacent pixels. As a result, firstly photons are registered under the wrong energy and, secondly photons can also be counted multiple times in adjacent pixels (=coincidence). These coincidences not only impair the spectral properties of the detector, but also lead quite generally to a deterioration of the DQE (detective quantum efficiency) of the detector due to an increase in the noise and a decrease in the spatial resolution. This is therefore an effect that degrades the image quality for all applications.

The typical circuit design approach to solving the problem consists in the implementation of so-called "charge summing" circuits in the evaluating electronics unit of the detector. Herein, during the detection process, in the analogue part of the evaluating electronics unit of a pixel, in particular, it is recognized that charge has been deposited in a plurality of adjacent pixels and the whole charge of all the pixels is assigned to one pixel (typically the pixel with the most charge or the fastest current rise). Thereby, double counting is prevented and the original charge is also almost restored. A disadvantage of such circuits is that the dead time of the pixels is hugely increased thereby. Thereby, the problem of the so-called "pulse pile-up", in which the signals of a plurality of photons become overlaid and also lead to falsified scans, is intensified. A good high flux capability, as required, for example, in computed tomography, is thus no longer available. Alternatively, by increasing the pixel size (e.g. to >0.3 mm edge length), the deterioration of the energy resolution and the DQE can be counteracted, although at the cost of the high flux capability and additionally at the cost of the spatial resolving power.

DE 10 2011 077 859 B4 discloses, for example, a quantum-counting radiation detector with an array of detector elements which each generate a charge quantity dependent upon the energy of incident radiation quanta and, to form relatively large detector units, are divided into groups of adjacent detector elements, a first processing stage, by which, for each of the groups, an electrical signal is provided which depends upon the sum of the generated charge quantities of the detector elements of the group, and a second processing stage by which the radiation quanta incident upon the respective groups are counted by evaluating the electrical signals provided, in order to obtain a count result for each group.

In "Coincidence counters for charge sharing compensation in spectroscopic photon counting detectors" by Scott S. Hsieh in IEEE Transactions on Medical Imaging (doi: 10.1109/TMI.2019.2933986), a coincidence counter bin is also proposed, the implementation of which resembles existing energy bins.

SUMMARY

At least one embodiment of the invention provides a possibility for an improved generating of X-ray image datasets taking account of coincidence information.

Further advantages and, partly per se inventive, embodiments and developments of the invention are disclosed in the claims and the description below.

At least one embodiment of the invention relates to a method for generating an X-ray image dataset via a photon-counting X-ray detector having a converter element which is configured to convert X-ray radiation into electrical signals. The X-ray detector has a multiplicity of pixel elements, each configured to form a count signal based upon a signal directly entering a pixel element of the multiplicity of pixel elements, and wherein at least one subset of the multiplicity of pixel elements is configured to form a coincidence count signal which is based upon the signal directly entering one pixel element of the subset of pixel elements and upon a coincidentally occurring signal of at least one further pixel element of the multiplicity of pixel elements. The method comprises at least first counting of at least one quantity of count signals dependent upon the incident X-ray radiation in each pixel element of the multiplicity of pixel elements;

second counting of at least one quantity of coincidence count signals in each pixel element of the subset of pixel elements with at least one further pixel element of the multiplicity of pixel elements; and generating an X-ray image dataset based upon the at least one quantity of count signals counted in each pixel element of the multiplicity of pixel elements and upon the at least one quantity of coincidence count signals counted in each pixel element of the subset of the multiplicity of pixel elements.

At least one embodiment of the invention further relates to an X-ray detector system, having at least one X-ray detector with a converter element, configured to convert X-ray radiation into an electrical signal, and having a multiplicity of pixel elements, each being configured to form a count signal based upon a signal directly entering a pixel element of the multiplicity of pixel elements and wherein at least a subset of the multiplicity of pixel elements is configured to form a coincidence count signal which is based upon the signal directly entering the pixel element of the subset of the multiplicity of pixel elements and upon a coincidentally occurring signal of at least one further pixel element of the multiplicity of pixel elements, and having a generating unit configured to generate an X-ray image dataset based upon at least one quantity of counting signals counted in each pixel element of the multiplicity of pixel elements and upon at least one quantity of coincidence count signals counted in each pixel element of the subset of the multiplicity of pixel elements.

At least one embodiment of the invention further relates to a medical imaging device comprising an X-ray detector system according to an embodiment of the invention. The medical imaging device can comprise, for example, a CT device, a C-arm X-ray device or an angiography X-ray device. Aside therefrom, other medical imaging devices which are configured to generate a two-dimensional or a three-dimensional image dataset of an object or patient on the basis of X-ray radiation are however also possible.

At least one embodiment of the invention further relates to a method for generating an X-ray image dataset via a photon-counting X-ray detector including a converter element, configured to convert X-ray radiation into an electrical signal, and including a multiplicity of pixel elements, configured to form a count signal based upon a signal directly entering a pixel element of the multiplicity of pixel elements and wherein at least a subset of the multiplicity of pixel elements is configured to form a coincidence count signal based upon a signal directly entering a pixel element of the subset of the multiplicity of pixel elements and upon a coincidentally occurring signal of at least one further pixel element of the multiplicity of pixel elements, the method comprising:

first counting of at least one quantity of count signals dependent upon the incident X-ray radiation in each pixel element of the multiplicity of pixel elements;

second counting of at least one quantity of coincidence count signals in each pixel element, of the subset of the multiplicity of pixel elements, with at least one further pixel element of the multiplicity of pixel elements; and generating an X-ray image dataset based upon the at least one quantity of count signals counted in each pixel element of the multiplicity of pixel elements and the at least one quantity of coincidence count signals counted in each pixel element of the subset of the multiplicity of pixel elements.

BRIEF DESCRIPTION OF THE DRAWINGS

The invention will now be described using example embodiments, making reference to the accompanying drawings. The illustrations in the figures are schematic, greatly simplified and not necessarily to scale. In the drawings:

FIG. 5 shows an illustration of a subpixel grid of subpixels overlapping with the pixel elements defined on the basis of the pixel grid of the multiplicity of pixel elements.

DETAILED DESCRIPTION OF THE EXAMPLE EMBODIMENTS

Figure 1:
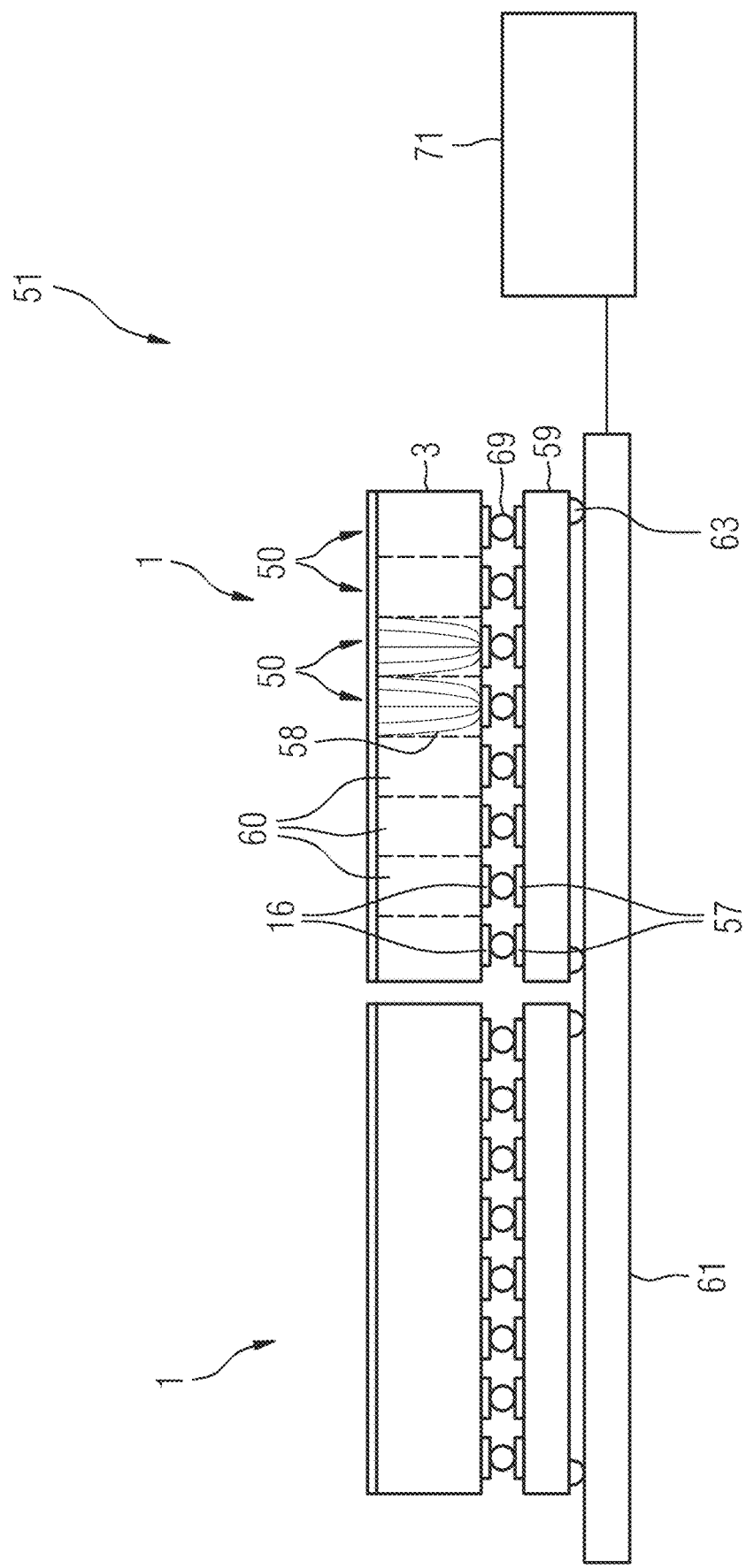
FIG. 1 shows an X-ray detector system having an X-ray detector with a multiplicity of pixel elements.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor;

however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for generating an X-ray image dataset via a photon-counting X-ray detector having a converter element which is configured to convert X-ray radiation into electrical signals. The X-ray detector has a multiplicity of pixel elements, each configured to form a count signal based upon a signal directly entering a pixel element of the multiplicity of pixel elements, and wherein at least one subset of the multiplicity of pixel elements is configured to form a coincidence count signal which is based upon the signal directly entering one pixel element of the subset of pixel elements and upon a coincidentally occurring signal of at least one further pixel element of the multiplicity of pixel elements. The method comprises at least first counting of at least one quantity of count signals dependent upon the incident X-ray radiation in each pixel element of the multiplicity of pixel elements;

second counting of at least one quantity of coincidence count signals in each pixel element of the subset of pixel elements with at least one further pixel element of the multiplicity of pixel elements; and generating an X-ray image dataset based upon the at least one quantity of count signals counted in each pixel element of the multiplicity of pixel elements and upon the at least one quantity of coincidence count signals counted in each pixel element of the subset of the multiplicity of pixel elements.

Advantageously, by way of the method according to at least one embodiment of the invention, through the provision of the coincidence information, taking account of the coincidence information in the generating step can be enabled and a reduction of the image quality of a generated X-ray image dataset based upon coincidences occurring in the pixel elements of the X-ray detector can be reduced. The implementation according to at least one embodiment of the invention thereby simultaneously permits negative effects on the high flux capability and extended dead times of the pixel elements to be prevented in that a time-consuming real time correction during the scan itself is avoided. Furthermore, the process chain for generating the X-ray image dataset can advantageously be adapted and possibly different correction methods or combinations of correction methods can be applied, based upon the quantities of coincidence count signals provided, possibly also subsequently and repeatedly, to the at least one quantity of counting signals counted in each pixel element or to a (preliminary) X-ray image dataset based thereon.

The subset of the multiplicity of pixel elements can thereby comprise the whole multiplicity of pixel elements. The multiplicity can, however, also comprise, apart from the subset of pixel elements, differently configured pixel elements. These can be configured, for example, merely to form and to count count signals. In that only a part of the pixel elements of the multiplicity of pixel elements is configured to form and count coincidence count signals, for example, a simplified circuit arrangement of the pixel elements can be enabled.

The at least one further pixel element of the multiplicity of pixel elements on which a coincidence count signal to be counted is based can be included by the at least one subset of the multiplicity of pixel elements, i.e. it can itself be part of the subset of the multiplicity of pixel elements. However, embodiments can also exist in which the at least one further pixel element is not part of the at least subset of the multiplicity of pixel elements.

In the context of the method according to at least one embodiment of the invention, more than one quantity of count signals can also be counted in a respective pixel element of the multiplicity of pixel elements. Likewise, more than one quantity of coincidence count signals can be counted in a respective pixel element of the subset of the multiplicity of pixel elements. The plurality of quantities of count signals and/or the plurality of quantities of coincidence count signals can then be included in the generating of the X-ray image dataset. For example, in each pixel element of the multiplicity of pixel elements, a plurality of quantities of count signals can be counted dependent upon a plurality of energy thresholds provided for energy-resolving scans. Similarly, in each pixel element of the subset of the multiplicity of pixel elements, a plurality of quantities of coincidence count signals can be counted dependent upon a plurality of energy thresholds provided for energy-resolving scans. Furthermore, in each pixel element of the subset of the multiplicity of pixel elements, a quantity or plurality of quantities of coincidence count signals can be counted dependent upon a plurality of further pixel elements of the multiplicity of pixel elements. Thus, whenever the at least one quantity of count signals or coincidence count signals is mentioned below, included therein can be also that, beyond this, further quantities can exist which can enter into the generating, counted in a similar way. Where coincidence information in general is mentioned below, included therein is the at least one quantity of coincidence count signals counted in each pixel element of the subset of the multiplicity of pixel elements and furthermore, if a plurality of quantities are counted, it can include the plurality of counted quantities of coincidence count signals. Additionally, the coincidence information ascertained can further comprise one or more quantities of coincidence count signals transferred from pixel elements of the subset of pixel elements to further pixel elements of the multiplicity of pixel elements. Where count information in general is mentioned below, included therein is at least the at least one quantity of count signals counted in each pixel element of the multiplicity of pixel elements and furthermore, if a plurality of quantities are counted, can include the plurality of counted quantities of count signals.

According to one embodiment variant of the method according to the invention, in the generating step, the at least one quantity of coincidence count signals counted in the pixel elements of the subset of the multiplicity of pixel elements enters into the data preprocessing before an image reconstruction, into the image reconstruction or into a post-processing step downstream of the image reconstruction.

The inventors have discovered that in each of the sub-steps, the coincidence information for corrections regarding the coincidences occurring can be used to enable an improved image quality. A combination of the three possibilities can also be provided. This means that the at least one quantity of coincidence count signals can enter both into the data preprocessing before an image reconstruction, as well as into the image reconstruction and/or into a postprocessing step downstream of the image reconstruction. Other combinations are also possible. Through the counting and thus the preparation of the coincidence information, a subsequent and repeated entry into, and also an entry into different processing stages of, the generating downstream of the scan process itself can be enabled.

The entry of the at least one quantity of coincidence count signals into the data preprocessing before an image reconstruction can comprise, for example, that at least in each pixel element of the subset of the multiplicity of pixel elements, the at least one quantity of count signals is adapted via the at least one quantity of coincidence count signals. The at least one quantity of coincidence count signals can be applied to the at least one quantity of count signals, whereupon advantageously, an adapted quantity of count signals is provided for the generating. Thereby, a correction of the quantities can be enabled in relation to coincidences that occur. The image reconstruction can then be based upon the adapted at least one quantity of count signals in each pixel element of the subset of pixel elements.

For example, at least in each pixel element of the subset of the multiplicity of pixel elements, the at least one quantity of coincidence count signals can be subtracted from the at least one quantity of count signals or added to the at least one quantity of coincidence count signals. A subtraction or addition can thereby comprise a weighted subtraction or addition. This means that just a portion or a multiple of the at least one quantity of coincidence count signals can be subtracted or added. However, other implementations can exist, via which at least one quantity of count signals can be adapted, for example, a multiplication, division or other, possibly also more complex, algorithms. Advantageously, quantities of count signals impaired by coincidences in the pixel elements can be directly and easily corrected and provided for the image reconstruction.

If a plurality of quantities of count signals are counted in the pixel elements, for example, dependent upon a plurality of energy thresholds, each or only a part of the quantities can be adapted with the aid of the ascertained coincidence information. If, similarly, a plurality of quantities of coincidence count signals is ascertained, for example, dependent upon a plurality of energy thresholds, different quantities of coincidence count signals can be used on different quantities of count signals for an adaptation.

For example, the step of generating can also comprise the use of a trained function, wherein the at least one quantity of coincidence count signals in at least one pixel element of the subset of the multiplicity of pixel elements enters into the trained function as input parameters. The trained function can be used, for example, in the step of preprocessing for an adaptation or correction of the quantities of count signals. The trained function can thereby be trained by a method of machine learning. In particular, the trained function can be a neural network, in particular, a convolutional neural network (CNN) or a network comprising a convolution layer.

A trained function maps input data to output data. For this purpose, the output data can further depend, in particular, upon one or more parameters of the trained function. The one or more parameters of the trained function can be ascertained and/or adapted by a training unit. The determination and/or the adaptation of the one or more parameters of the trained function can be based, in particular, upon a pair made from training input data and associated training output data, wherein the trained function is applied to the training input data to generate output data. In general, a trainable function, i.e. a function with one or more parameters not yet adapted, can also be designated a trained function.

Other expressions for trained function are trained mapping rule, mapping rule with trained parameters, function with trained parameters, algorithm based upon artificial intelligence, algorithm of machine learning. An example of a trained function is an artificial neural network wherein the edge weights of the artificial neural network correspond to the parameters of the trained function. In place of the expression "neural network", "neural net" can also be used. In particular, a trained function can also be a deep neural network (or deep artificial neural network). Other algorithms of machine learning, in particular, are also usable as a trained function. The trained function can be trained, for example, by way of a back-propagation. The training input data can comprise, for example, a multiplicity of measured and/or simulated training image datasets having an impairment due to coincidences occurring. The training output data can comprise, for example, measured and/or simulated training image datasets in which coincidences have been suppressed, for example, by suitable pixel circuits or by suitable assumptions in the simulation.

By applying an artificial intelligence system, i.e. a trained function, all the relevant influence variables for the application of the coincidence information can be taken into account, including those for which a user cannot guess any relationship. In particular, via a trained function, after the training phase, a correction of the count signals can be enabled automatically, particularly reliably and time-efficiently with the aid of the coincidence count signals.

The entry of the ascertained at least one quantity of coincidence count signals can also be carried out before a transfer of the ascertained at least one quantity of count signals from an X-ray detector to a generating unit, which is configured for an image reconstruction or only after a transfer of the count signals from the X-ray detector to a generating unit. This means that the coincidence information can be applied in the context of an "on-board processing" to the at least one quantity of count signals, so that only the adapted at least one quantity of count signals must be read out from the X-ray detector and transferred to the generating unit. In this way, transfer bandwidth can advantageously be spared.

The entry of the at least one quantity of coincidence count signals into the image reconstruction of the X-ray image dataset can comprise, for example, that the coincidence information enters an iterative reconstruction algorithm. For example, the coincidence information can be used in the forward projection in the context of a model-based iterative reconstruction and can contribute to an improved image reconstruction through the provision of the additional information. Other types of possibility can also exist.

The entry of the at least one quantity of coincidence count signals in each pixel element into a postprocessing step downstream of the image reconstruction can comprise, for example, that both on the basis of the ascertained coincidence information, coincidence image data and also on the basis of the count information, preliminary image data is generated by a reconstruction algorithm. The coincidence image data can then be used on the preliminary image data for improving the image quality in order to generate a final, improved X-ray image dataset.

According to one variant embodiment of the method, it can be provided that, based upon the at least one quantity of count signals counted in each pixel element of the multiplicity of pixel elements, a preliminary image dataset is generated, and that, based upon the at least one quantity of counted coincidence count signals in each pixel element of the subset of the multiplicity of pixel elements, a coincidence image dataset is generated which is applied to the preliminary image dataset in the step of generating the X-ray image dataset. A particularly simple variant of the application can thereby comprise, for example, a linear combination of the coincidence image data with the preliminary image data. Apart therefrom, other implementations are however also possible.

Advantageously, a first preliminary image dataset can be provided promptly. Advantageously, according to need, for example, after a first assessment of the preliminary image dataset and variably based upon the reconstructed image data, an improvement of the image quality can be enabled by way of the coincidence information. Advantageously, the allocation of previously reconstructed image datasets can enable a robust and time-efficient provision of the final image dataset, which has an improved image quality.

In a further embodiment of the method according to the invention, each pixel element of the multiplicity of pixel elements has a quantity of comparators, each with an adjustable energy threshold, wherein in each pixel element of the multiplicity of pixel elements, based upon a starting signal of at least one comparator of the quantity of comparators of each pixel element, the at least one quantity of count signals is counted.

Each pixel element of the multiplicity of pixel elements has at least one comparator with an adjustable energy threshold. Each pixel element of the multiplicity can have a plurality of comparators, each with an adjustable energy threshold. The output signal of each comparator of the quantity of comparators can then correspond to the count signal, which is counted by a counter, also called a counting element, coupled in a signal-carrying manner to the respective comparator. However, the count signal can also be based upon a further processed or adapted output signal. For example, an element for preventing paralysis with high X-ray fluxes can be connected between the signal output of the comparator and the counting element, which on sustained exceeding of the comparator threshold induces further counting events which can be counted via the counting element. The quantity of count signals can also be stored by the counting element, at least provisionally, until a readout of the counter value.

Additionally, in a respective pixel element of the subset of the multiplicity of pixel elements, based upon the output signal of at least one comparator of the quantity of comparators of the respective pixel element of the subset of the multiplicity of pixel elements and at least upon the output signal of a comparator of the quantity of comparators of the at least one further pixel element of the multiplicity of pixel elements, the at least one quantity of coincidence count signals is counted. The at least one comparator of the quantity of comparators of the respective pixel element of the subset of the multiplicity of pixel elements, upon which the coincidence count signal is based, can correspond to that comparator of the quantity of comparators upon which the count signal in the pixel element of the subset is based. The coincidence count signal and the count signal, the quantities of which are counted in the respective pixel element of the subset of the multiplicity of pixel elements can, however, also be based upon output signals of different comparators of the respective pixel element.

For the formation of the coincidence count signals, the comparator of the quantity of comparators of the respective pixel element of the subset of pixel elements and the comparator of the quantity of comparators of the at least one further pixel element of the multiplicity of pixel elements upon which the coincidence count signal is based, can be linked therefor in a signal-carrying manner to a coincidence logic unit. The coincidence logic unit can be configured to provide, on occurrence of at least two coincidentally occurring signals, an output signal which can be counted by a counter coupled in a signal-carrying manner to the coincidence logic unit as a coincidence count signal.

The counting of the count signals and the counting of the coincidence count signals based upon the output signals from at least one comparator of a respective pixel element represents an advantageously suitable possibility for providing the coincidence or count information necessary for generating an improved X-ray image dataset, which information prevents unnecessary dead times of the X-ray detector.

Preferably, the X-ray detector is also configured for energy-resolved scans and has more than one, for example two, three, four or more comparators, each with an adjustable energy threshold, wherein based upon the output signals from more than one comparator, a quantity of count signals can be counted in each case. In this variant, each pixel element of the multiplicity of pixel elements comprises a plurality of comparators, wherein based upon the respective output signals from more than one comparator, a quantity of count signals based upon the output signals associated therewith can be counted. Advantageously, based upon the plurality of quantities of count signals, an energy-resolved X-ray image dataset can be generated.

Additionally, a plurality of quantities of coincidence count signals, based upon the output signals from a plurality of comparators of the quantity of comparators of the respective pixel element of the subset of the multiplicity of pixel elements, and at least upon the output signal of a comparator of the quantity of comparators of the at least one further pixel element of the multiplicity of comparators can be counted. This means that each pixel element of the subset of the multiplicity of pixel elements can have a plurality of comparators, wherein based upon the respective output signals from more than one comparator, in each case, at least one quantity of coincidence count signals is counted with at least one further pixel element of the multiplicity of pixel elements.

Advantageously, a more detailed item of coincidence information can lead, dependent upon a plurality of energy thresholds, to an improved correction and to extended correction possibilities which would not be accessible through the provision of only a single quantity of coincidence count signals. Thus, on provision of a plurality of energy thresholds, the plurality of quantities of count signals based thereupon can be better corrected via a plurality of coincidence count signals dependent upon the same energy thresholds. Additionally, the evaluation of more detailed coincidence information in the form of a plurality of quantities of coincidence count signals dependent upon a plurality of energy thresholds can better reveal indications of a spatial information item regarding incident X-ray photons or an improved spectral information item regarding the incident X-ray photons and, thereby, enhanced correction possibilities.

According to another embodiment of the method according to the invention, for the second counting of the at least one quantity of coincidence count signals, the adjustable energy threshold of the at least one comparator of the quantity of comparators of the respective pixel element of the subset of the multiplicity of pixel elements and the adjustable energy threshold of the at least one comparator of the quantity of comparators of the at least one further pixel element of the multiplicity of pixel elements on which the coincidence count signals are based, has an identical energy threshold value. This means in essence that coincidence count signals are counted which are based upon coincidentally occurring signals which, both in the respectively observed pixel element of the subset of the multiplicity of pixel elements and also in the at least one further pixel element of the multiplicity of pixel elements each having an energy threshold, have exceeded the same energy threshold. This can also be denoted an (energy-)symmetrical exceeding of energy thresholds or an (energy-)symmetrical coincidence in the pixel under consideration and the at least one further pixel element.

Advantageously, the access to (energy-)symmetrical exceeding of energy thresholds by coincidentally occurring signals permits corrections with an acceptable circuit design effort, which corrections enable the achievement of a markedly improved image quality of an X-ray image dataset, for example an improved noise level. For example, the coincidence information regarding symmetrical exceeding of energy thresholds permits, in a simple manner, an adaptation of the at least one counted quantity of count signals in the pixel elements, so that double counting of photon events can be corrected to a large extent.

On provision of a plurality of comparators, each with one adjustable energy threshold, at least one symmetrical coincidence regarding the lowest energy threshold can be taken into account. At least one quantity of coincidence count signals can be counted, dependent upon the at least one comparator, adjusted to the lowest energy threshold, of the quantity of comparators of the respective pixel element of the subset of the multiplicity of pixel elements and the at least one comparator, adjusted to the lowest energy threshold, of the quantity of comparators of the at least one further pixel element. The coincidence information regarding the symmetrical exceeding of the lowest energy threshold can advantageously reflect the quantity of all coincidences occurring between the participating pixel elements. However, only improvement possibilities are available on the basis thereof and no suggestion of an improved assignment of the coincidences to a specific pixel element can be derived in this way.

The information regarding symmetrical exceeding of the energy thresholds can also be advantageously utilized to improve the spectral information of the data. Underlying this is the concept that the probability of coincidences is greater for higher energy photons than for lower energy photons. From this it follows that these photons are counted multiple times in the lower energy thresholds and are therefore more highly weighted. With the entry of the coincidence information into the generating, it can advantageously be reduced by a corresponding correction. For example, the correction can comprise a redistribution of the counted quantities based upon at least one portion of the counted symmetrical coincidences, i.e. at least one portion of the counted quantity of coincidence count signals based upon a symmetrical exceeding, to a higher-energy threshold.

In one variant embodiment of the method according to the invention, it can be provided that for the second counting of the at least one quantity of coincidence count signals, the adjustable energy threshold of the at least one comparator of the quantity of comparators of the respective pixel element of the subset of the multiplicity of pixel elements and the adjustable energy threshold of the at least one comparator of the quantity of comparators of the at least one further pixel element of the multiplicity of pixel elements, on which the coincidence count signals are based, have different energy threshold values. This means in essence that coincidence count signals are counted which are based upon signals which, in the respective pixel element of the subset of pixel elements, have exceeded an energy threshold with a different energy threshold value, for example, a higher-energy or a lower-energy threshold than in the at least one further pixel element of the multiplicity of pixel elements. For example, a coincidence count signal can be formed based upon a comparator of the respective pixel element of the subset of pixel elements having an energy threshold with a first energy threshold value and a comparator of the further pixel element of the multiplicity of pixel elements having a second energy threshold value. This can also be denoted an (energy-) asymmetrical exceeding of energy thresholds or an (energy-) asymmetrical coincidence in the pixel element under consideration, and at least one further pixel element.

Advantageously, the access to (energy-)asymmetrical exceeding of energy thresholds by coincidentally occurring signals permits improved indications of a spatial information item regarding incident X-ray radiation. This means that an indication of the pixel element in which a majority of the energy of an X-ray photon has been deposited can be better derived. Advantageously, based thereon, further improvements of the image quality, which include the possibility of better localization, can be enabled. Advantageously, the quantities of coincidence count signals which are based upon different energy thresholds can be utilized particularly advantageously to achieve an improved spatial resolution.

In an advantageous embodiment of the invention, it is also provided that in each pixel element of the subset of pixel elements, both at least one quantity of coincidence count signals which is based upon the same energy threshold value is counted, and at least one quantity of coincidence count signals is counted which is based upon different energy threshold values.

This embodiment variant advantageously provides a particularly detailed item of coincidence information, wherein a combined entry of the coincidence information regarding an (energy-)symmetrical or (energy-)asymmetrical exceeding of energy thresholds can be utilized particularly advantageously in the generating, for the improvement of the image quality.

In preferred embodiment variants, coincidence count signals are formed in each pixel element of the subset of pixel elements with between one and 24 further pixel elements of the multiplicity of pixel elements. Preferably, the at least one further pixel element comprises, in the usually orthogonal matrix-like pixel grid generated by the arrangement of the multiplicity of pixel elements, at least one directly adjacent pixel element of the respective pixel element of the subset of pixel elements or a diagonally adjacent pixel element of the multiplicity of pixel elements.

Advantageously, coincidence count signals are formed at least with those further pixel elements in which coincidental signals occur with a high probability. This can comprise at least the four directly adjacent pixel elements or the four directly adjacent pixel elements together with the diagonally adjacent pixel elements. For example, coincidence count signals are formed in each pixel element of the subset of the multiplicity of pixel elements at least with the four directly adjacent further pixel elements of the multiplicity of pixel elements. However, another selection and/or quantity of further pixel elements can be provided. For example, next but one neighbors, i.e. pixel elements adjacent to the pixel elements directly adjacent to the pixel element under consideration, can be considered regarding coincidentally occurring signals. The consideration and inclusion of next but one neighbors can be advantageous, in particular, when it is provided to group together signals form a plurality of pixel elements for generating the X-ray image dataset, or with small pixel sizes wherein coincidentally occurring signals are also to be expected to a large extent beyond the spacings defined by the pixel elements.

The quantity and selection of further pixel elements upon which the coincidence count signal is based can vary within the subset of the multiplicity of pixel elements. However, a more complex circuit arrangement among the pixel elements is associated with a larger quantity of further pixel elements.

According to a further embodiment of the method according to the invention, coincidence count signals are formed in each pixel element of the subset of pixel elements with between one and 24 further pixel elements of the multiplicity of pixel elements, wherein the at least one quantity of coincidence count signals counted in the step of the second counting for each pixel element of the subset of pixel elements is based upon coincidentally occurring signals of all further pixel elements.

In this embodiment, each quantity of coincidence count signals counted in a pixel element of the subset of pixel elements can correspond to the sum of the coincidence count signals formed in the one to 24 further pixel elements. This means that the respective quantity of coincidence count signals is increased by one count unit when a coincidental signal occurs in at least one of the one to 24 further pixel elements. Behind this lies the recognition that the quantity of the coincidences of one pixel element with any neighbors can already convey a large part of the information that can advantageously be used for corrections. At the same time, a simple signal-carrying circuit arrangement can thereby be ensured.

Alternatively, in a further embodiment of the method according to the invention, it can be provided that coincidence count signals are formed in each pixel element of the subset of the multiplicity of pixel elements with between one and 24 further pixel elements of the multiplicity of pixel elements, wherein in the step of the second counting, at least one quantity of coincidence count signals is counted with each of the further pixel elements.

In this embodiment, in the pixel element of the subset of the multiplicity of pixel elements, for each of the further pixel elements individually, at least one quantity of coincidence count signals is counted. Advantageously, the most detailed possible pixel-specific coincidence information item is available which carries an item of directional information of the coincidences occurring, relative to the pixel element under consideration of the subset of pixel elements. This detailed, pixel-specific coincidence information item can be used particularly advantageously for an improved spatial information item, i.e. an improved localization of the origin of the counted signals occurring. However, an increased signal-carrying technical effort and an increased data quantity to be transferred, possibly from an X-ray detector, is associated therewith.

In a further embodiment variant of the method, the method also comprises transferring at least one quantity of coincidence count signals counted in a pixel element of the subset of the multiplicity of pixel elements to at least one of the further pixel elements with which a coincidence count signal is formed in the respective pixel element of the subset, wherein the step of generating is further based upon the at least one transferred quantity of coincidence count signals.

Underlying this variant, in particular, is the concept that the coincidence information can apply between participating pixel elements as (pixel-)symmetrical. If, in a first pixel element of the subset of the multiplicity, a quantity of coincidence count signals of a pixel element is counted with a second pixel element of the multiplicity, the counted quantity can also be transferred to the second pixel element and utilized in the second pixel element for a corresponding quantity of coincidence count signals of the second pixel element with the first pixel element.

This variant permits, for pixel elements of the multiplicity of pixel elements which are not part of the subset of the multiplicity of pixel elements, quantities of coincidence count signals to be ascertained and coincidence information to be collected which can be used in the method for generating an X-ray image dataset and its variants in a similar manner as a counted quantity of coincidence count signals can be utilized. For example, in a matrix-like arrangement of the multiplicity of pixel elements, only every second pixel element of the multiplicity can be part of the subset and thus be configured to count at least one quantity of coincidence count signals. For the remainder of the multiplicity of pixel elements, a transfer of the coincidence information can then take place.

This variant also permits a redundant counting of coincidence count signals in the pixel elements of the subset of the multiplicity of pixel elements to be reduced or the collected coincidence information in a pixel element of the subset of the multiplicity to be extended. The coincidence information ascertained in a pixel element of the subset of the multiplicity of pixel elements can be extended or completed by way of a transfer without this quantity having to be counted in the pixel element itself. For example, each pixel element of the multiplicity can count a quantity of coincidence count signals with its northern adjacent pixel. The coincidence information of each pixel element regarding its southern neighbor is then accordingly situated correspondingly in the southern adjacent pixel element and can be transferred to the respective pixel element for the application of the method for generating. In this way, in each pixel element of the subset itself, only a portion of the coincidence information desired for a method for generating an X-ray image dataset can be counted, wherein through the transfer, a completion can be enabled. Advantageously thereby, the complexity in the signal-carrying circuit arrangement of the pixel elements can be simplified.

A quantity transferred to a pixel element of the multiplicity of pixel elements can be utilized in the method for generating an X-ray image dataset and its variants in a similar manner as for a counted quantity. Thus, where a quantity of coincidence count signals or coincidence information are mentioned below, this can comprise a counted and/or a transferred quantity of coincidence count signals, without this being explicitly differentiated in the text. A transferred quantity of coincidence information can enter, in the generating step, into the data preprocessing before an image reconstruction, into the image reconstruction, or into a postprocessing step downstream of the image reconstruction. For example, a quantity of coincidence count signals transferred to a pixel element can be utilized to adapt a counted quantity of count signals in this pixel element. For example, at least one quantity of coincidence count signals transferred to a pixel element can be subtracted from a quantity of count signals counted in the pixel element or added to the at least one quantity of count signals. For example, a coincidence image dataset can also be based upon a transferred quantity of coincidence count signals. For example, a transferred quantity of coincidence count signals can also enter into a trained function as an input parameter. For example, a transferred quantity of coincidence count signals can enter the image reconstruction.

Preferably, an item of pixel-specific coincidence information underlies a transferred quantity, wherein the quantity to be transferred is based upon coincidence count signals which are formed only between the pixel element from which the quantity is transferred and the pixel element to which the quantity is transferred. This means that in this variant, in the step of the second counting, at least one respective quantity of coincidence count signals is counted with each of the further pixel elements, provided a plurality of further pixel elements is provided for forming coincidence count signals. In this way, a clearer assignment is possible and a direct correspondence of the quantities can be better guaranteed.

However, variants of the method can exist wherein provided a plurality of further pixel elements is provided for the formation of coincidence count signals, a quantity of coincidence count signals is transferred which is based upon coincidentally occurring signals of all the further pixel elements. This means that the transferred quantity of coincidence count signals can correspond to the sum of the coincidence count signals formed with the further pixel elements. Underlying this can be the assumption that at least for pixel elements which are arranged in close proximity to the pixel element from which a quantity is transferred and which are therefore subject to similar conditions, also based upon a sum, at least an estimate of a quantity of coincidence count signals which can be applied in a method for generating an X-ray image dataset can be possible. In a development of this variant, it can be provided, for example, that in the step of transferring, a trained function is applied which enables an optimized estimate of the transferred quantities based upon sum quantities, for example, also taking account of the counted quantities of count signals and of the relative arrangement of the pixel elements to one another. Such a trained function can be trained, for example, via training data comprising an item of pixel-specific coincidence information and a summed item of coincidence information, so that after training, the pixel-specific coincidence information can be estimated by way of the trained function.

In a variant of the method, for each pixel element of the multiplicity of pixel elements, at least one counted or one transferred quantity of coincidence count signals is ascertained. Advantageously, coincidence information ascertained in each pixel element of the multiplicity of pixel elements can be made available so that optimal conditions can be provided for the generating of the X-ray image dataset.

In a further embodiment of the method according to the invention, a first matrix-like pixel grid is defined by the arrangement of the multiplicity of pixel elements. In the step of generating, based upon the pixel grid, a subpixel grid of subpixels overlapping with the pixel elements of the multiplicity of pixel elements is defined, wherein the subpixel grid has a reduced grid spacing, at least along one grid dimension, relative to the pixel grid.

In a general case, the original pixel grid $A_1 \times A_2$ can be transferred to a new subpixel grid $B_1 \times B_2$ where $B_1 \geq A_1$ and $B_2 \geq A_2$, wherein for at least one of the relations $B > A$ applies. $A_1$ and $A_2$ or $B_1$ and $B_2$ each define the quantity of the pixel elements in the pixel grid or the quantity of subpixels in the subpixel grid along the two spatial dimensions of the respective grid. This means that at least one dimension of the subpixel grid is displayed finer than the pixel grid. The grid spacing can, however, vary along the grid dimensions.

Furthermore, at least one virtual quantity of count signals is assigned to each subpixel, wherein the respective at least one virtual quantity of at least one portion of the subpixels is based upon at least one counted or transferred quantity of coincidence count signals of a pixel element overlapping with the respective subpixel. Based upon the virtual quantity of count signals assigned to the virtual subpixels, the X-ray image dataset is generated.

This variant proceeds, according to an embodiment of the invention, from the at least one quantity of coincidence count signals in the pixel elements of the subset of the multiplicity of pixel elements being counted or ascertained individually with each of the linked further pixel elements. This means that for the assignment of the virtual quantity, a (counted or transferred) pixel-specific coincidence information can be made available. A pixel-specific coincidence information item contains an item of directional information regarding the coincidences and thus the possibilities of an improved localization of the coincidences occurring.

Preferably, the at least one quantity of coincidence count signals is also counted with at least one of the directly adjacent pixel elements.

The at least one virtual quantity of count signals can thereby be based, for at least one quantity of the subpixels only upon at least one counted or transferred quantity of coincidence count signals of a pixel element overlapping with the respective subpixel. The at least one virtual quantity of count signals can also be based upon at least one portion of coincidence counts signals and upon at least one quantity of count signals of a pixel element overlapping with the respective subpixel. An assigned virtual quantity can also be based only upon at least one quantity of count signals and an overlapping pixel element.

Advantageously, the direction information of the ascertained coincidence information can be utilized for an improved transfer of the quantities to the virtual subpixels and thus enable an improved spatial resolution.

It is thereby preferably provided that the virtual quantity of count signals assigned to a respective subpixel is dependent upon the relative position of the virtual subpixel to a pixel element overlapping the subpixel. Behind this is the assumption that the coincidence information with an item of directional information can be utilized for an improved localization of the count signals on a finer subpixel grid. It is thus assumed that all the photons which meet a pixel element in the pixel grid centrally (and thus with a greater probability, generate no coincidental signals in the further pixel element), can be assigned to a subpixel accordingly centrally overlapping the pixel element under consideration. By contrast, coincidence events can be assigned to those subpixels which overlap the original pixel element closer to the edge or lie, for example, between two original pixel elements.

In method variants, it can be provided that the virtual quantity of count signals assigned to one subpixel is dependent, in particular, upon the relative spacing of the virtual subpixel from the center of an overlapping pixel element. Thereby, for example, coincidence count signals which result from a symmetrical exceeding are assigned to subpixels and which have a greater spacing from the center of the overlapping pixel element and such coincidence count signals which result from an asymmetrical exceeding are assigned to subpixels which have a relatively smaller spacing from the center of the overlapping pixel element. Advantageously, an improved localization of the count signals in the subpixel grid and thus an improved spatial resolution can thereby be enabled.

In the method variant, it can be provided that the area of the virtual subpixels in the subpixel grid is identical. Advantageously, a suitable and simple implementation is provided which enables a time-efficient provision of the X-ray image dataset.

It can further be provided thereby that the area of the virtual subpixels in the subpixel grid differs. Advantageously, a more flexible implementation can be provided which enables further boundary conditions or assumptions for an improved localization of the counted quantities.

It can be provided in the selection of the subpixel sizes of the subpixel grid, for example, that the pixel size, i.e. the pixel area of the subpixels is selected dependent upon at least one physical parameter. The physical parameter can be linked, in particular, to the charge distribution generated in the converter element by the incident X-ray radiation. By including assumptions regarding, for example, the diameter of the charge cloud generated or the extent of the fluorescences, in the selection of the pixel area, advantageously, a qualitatively higher image quality can be enabled. Advantageously, the most constant possible relationship of statistics to pixel area in the subpixel grid can be achieved in order to enable an even and high quality image impression.

At least one embodiment of the invention further relates to an X-ray detector system, having at least one X-ray detector with a converter element, configured to convert X-ray radiation into an electrical signal, and having a multiplicity of pixel elements, each being configured to form a count signal based upon a signal directly entering a pixel element of the multiplicity of pixel elements and wherein at least a subset of the multiplicity of pixel elements is configured to form a coincidence count signal which is based upon the signal directly entering the pixel element of the subset of the multiplicity of pixel elements and upon a coincidentally occurring signal of at least one further pixel element of the multiplicity of pixel elements, and having a generating unit configured to generate an X-ray image dataset based upon at least one quantity of counting signals counted in each pixel element of the multiplicity of pixel elements and upon at least one quantity of coincidence count signals counted in each pixel element of the subset of the multiplicity of pixel elements.

The subset of pixel elements can comprise the whole multiplicity of pixel elements. The multiplicity can, however, also comprise, apart from the subset of pixel elements, differently configured pixel elements.

The X-ray detector system can, in particular, also be configured to carry out a method according to one of the method embodiment variants described above in that the X-ray detector and the generating unit are configured to carry out the method and its aspects.

At least one embodiment of the invention further relates to a medical imaging device comprising an X-ray detector system according to an embodiment of the invention. The medical imaging device can comprise, for example, a CT device, a C-arm X-ray device or an angiography X-ray device. Aside therefrom, other medical imaging devices which are configured to generate a two-dimensional or a three-dimensional image dataset of an object or patient on the basis of X-ray radiation are however also possible.

The advantages of the method and its embodiments and variants can also be transferred directly to the X-ray detector system and the medical imaging device.

In the context of at least one embodiment of the invention, features which are described in relation to different embodiments of the invention and/or different claim categories (method, use, apparatus, system, arrangement etc.) can, in particular, be combined to further embodiments of the invention. For example, a claim which relates to an apparatus, can also be developed with features which are described or claimed in relation to a method and vice versa. Functional features of a method can be carried out by way of correspondingly configured object components. Apart from the embodiments of the invention expressly described in this application, many further embodiments of the invention are conceivable, at which the skilled person can arrive without departing from the field of the invention as disclosed by the claims.

The use of the indefinite article "a" or "an" does not preclude the relevant feature also being present plurally. The use of the expression "have" does not preclude the concepts linked by way of the expression "have" being identical. For example, the medical imaging device has the medical imaging device. The use of the expression "unit" does not preclude the subject matter to which the expression "unit" relates being able to have a plurality of components that are spatially separated from one another.

The expression "based upon" can be understood in the context of the present application, in particular, in the sense of the expression "using". In particular, a formulation as a result of which a first feature is generated (alternatively: ascertained, determined, etc.) based upon a second feature does not preclude the first feature being generated (alternatively: ascertained, determined, etc.) based upon a third feature.

FIG. 1 shows schematically an example X-ray detector system 51 in a side view, designed to carry out a method according to the invention and having an X-ray detector 1 with a multiplicity of pixel elements 50.

The X-ray detector system 51 shown by way of example in FIG. 1 has two visible X-ray detectors 1 in the side view illustrated. An X-ray detector system 51 can, however, also have only one X-ray detector 1 or more than two X-ray detectors 1. In an advantageous embodiment, the X-ray detector system 51 has an arrangement of a plurality of X-ray detectors 1 in the form of a two-dimensional matrix. Each of the X-ray detectors 1 can itself have a two-dimensional, matrix-like arrangement of the multiplicity of pixel elements 50 assigned to an X-ray detector 1. The quantity of the multiplicity of pixel elements 50 can be, for example, in the range from 100 to several thousands.

The X-ray detector 1 used in the context of the invention can also be designated a (photon)-counting or direct-conversion X-ray detector 1. The X-ray detector 1 shown has a converter element 3. The converter element 3 can be configured as an extensive direct converter having, for example, CdTe, CZT, CdZnTeSe, CdTeSe, CdMnTe, InP, TlBr$_2$, HgI$_2$, GaAs, Si, amorphous selenium (a-Se) or other substances as the converter material. On the upper side, the converter element 3 has a first electrode 18 (also named top electrode). The lower side of the converter element 3 has a plurality of sensor pixel electrodes 16. Each sensor pixel electrode 16 is connected in the example X-ray detector 1 shown here via (electrically) conductive connections 69 and evaluating pixel electrodes 57 to a pixel-specific pixel electronics unit of the pixel elements 50 in the evaluating unit 59. The pixel-specific pixel electronics unit is configured for a pixel-wise processing of the signals received due to the incident X-ray radiation. The evaluating unit 59 can be configured, for example, in the form of an ASIC (Application-Specific Integrated Circuit). The conductive connections 69 can be configured, for example, as solder balls (bump bonds) or solder material in conjunction with copper pillars or by other means.

In other embodiment variants, the connection can also be configured differently, for example, in the form of a conducting adhesive connection or the like. The combined number of sensor pixel electrodes 16, the number of conductive connections 69, the number of evaluating pixel electrodes 57, the number of pixel-specific pixel electronics units in the evaluating unit 59 and the number of pixel elements 50 of an X-ray detector 1 are usually identical. The electric field, indicated by the field lines 58, between the top electrode 18 and the sensor pixel electrode 16 defines a sensitive detection volume 60 assigned to each pixel element 50 of the X-ray detector 1 in the converter element 3, indicated by the dashed lines in the converter element 3. The unit consisting of a sensor pixel electrode 16, a conductive connection 69, a pixel electrode 57, a pixel-specific pixel electronics unit in the evaluating unit 59 and possibly an associated detection volume 60 can be designated a pixel element 50, also called a detection element.

The evaluating unit 59 is further connected in this example embodiment, via connections 63 and a peripheral electronics unit 61, to a generating unit 71. The peripheral electronics unit 61 can serve, for example, to collect the measured data of the plurality of evaluating units 59 and possibly also a pre-processing of the measured data before a transfer to the generating unit 71.

Additionally, the X-ray detector 1 or the X-ray detector system 51 can also comprise further components, not shown here.

Incident X-ray radiation is converted in the converter material of the converter element 3, dependent upon the energy locally deposited by the incident X-ray radiation, into charge carriers, i.e. into an electrical signal, based upon which, in the pixel-specific pixel electronics unit of that pixel element 50 in the associated detection volume 60 of which charge carriers have been generated, a signal, typically an electrical pulse, for example, a charge pulse, is generated and processed. The evaluating unit 59 provides pixel-specific pixel electronics units for the pixel-wise processing of a signal directly arriving via the sensor pixel electrodes 16 or pixel electrodes 57 of a respective pixel element 50.

In a photon-counting X-ray detector 1, typically an electrical pulse is generated, the size and/or length of which corresponds to the energy of the incident X-ray quantum deposited in the converter material. The electrical pulse is then registered as a counting event in a pixel element 50 and classified into a digital storage unit of a counter 13, also designated a counting element 13, i.e. counted as a (pixel) count signal if the electrical pulse generated in the pixel element 50 lies above a defined threshold value, i.e. an adjustable energy threshold S in the pixel electronics unit of the pixel element 50. In other words, if the generated signal exceeds the energy threshold S as set in a pixel element 50, the counter value of the counting element 13 linked thereto of the pixel element 50 is incremented by one count unit.

The adjustable energy threshold S can typically be adjusted to an energy threshold value via a comparator 19. The energy threshold value of an energy threshold S can, in principle, also be firmly defined by analogue means, but is typically applied via e.g. a DAC (digital-to-analogue converter) and is thus variably adjustable in a particular range. The energy threshold S can be adjustable either pixel-wise locally (via the comparator and the DAC), for groups of pixel elements, or also globally in the X-ray detector 1 for all pixel elements 50 of the X-ray detector 1. In the event that two, three or more adjustable energy thresholds S are provided in a pixel element 50 for energy-resolved scans, the electrical signal generated is classified according to the different, pre-defined energy thresholds S in one or more counting elements 13 which are each linked to an energy threshold S, i.e. counted.

Through charge-sharing or fluorescences, a distribution of the deposited energy of a single event, i.e. an incident X-ray photon, to two or more pixel elements 50, or their detection volumes 60, can occur. This means that charge carriers can be generated in detection volumes 60 which are assigned to more than one pixel element 50. It can accordingly arise that an incident photon generates coincidental signals in more than one pixel element 50 and that multiple counts occur in a plurality of pixel elements 50. Such multiple counts can lead to disturbance effects in the X-ray image dataset, for example, an increased noise level, reduced spatial resolution and/or a reduced energy resolution.

The multiplicity of pixel elements 50 of the X-ray detector 1 according to the invention is now configured in each case to form a count signal based upon a signal directly entering a pixel element 50 of the multiplicity of pixel elements 50 and based thereon, to count at least one quantity T of count signals. At least a subset of the multiplicity of pixel elements 50 of the X-ray detector 1 according to the invention is respectively also configured to form a coincidence count signal and, based thereon, to count at least one quantity C of coincidence count signals. Therein, a coincidence count signal formed in a respective pixel element 50 of the subset of the multiplicity of pixel elements 50 is based upon a signal directly entering the respective pixel element 50 of the subset of pixel elements 50, and upon a coincidentally occurring signal of at least one further pixel element 50 of the multiplicity of pixel elements 50. The at least one further pixel element 50 of the multiplicity of pixel elements 50 on which a coincidence count signal is based can, but does not necessarily have to, be comprised by the at least one subset of the multiplicity of pixel elements 50.

The at least subset of the multiplicity of pixel elements 50 can further comprise the whole multiplicity of pixel elements 50. This means that the X-ray detector 1 can have a multiplicity of pixel elements 50, wherein each pixel element 50 of the multiplicity can be configured to form a count signal and a coincidence count signal. The multiplicity of pixel elements 50 can, however further comprise, apart from the subset of the multiplicity of pixel elements 50, differently designed pixel elements 50. These can be configured, for example, merely to form and to count count signals.

In the event that two, three or more adjustable energy thresholds S are provided in a respective pixel element 50 of the multiplicity of pixel elements 50 for energy-resolved scans, a respective pixel element 50 of the multiplicity of pixel elements 50 can be configured accordingly also to count a plurality of quantities T of count signals dependent upon the energy thresholds S provided as set. Similarly, the inventive X-ray detector 1 or a respective pixel element 50 of the subset of the multiplicity of pixel elements 50 can be configured to count a plurality of quantities C of coincidence count signals, for example, dependent upon the energy thresholds S involved and/or dependent upon the further pixel element(s) 50 involved.

The generating unit 71 is configured, based upon the at least one quantity T of count signals counted in the multiplicity of pixel elements 50 and upon the at least one quantity C of coincidence count signals counted in each pixel element 50 of the subset of the multiplicity of pixel elements 50, to generate an X-ray image dataset.

The generating unit can also be configured to transfer at least one quantity of coincidence count signals counted in a pixel element 50 of the subset of the multiplicity of pixel elements 50 to at least one of the further pixel elements 50 with which a coincidence count signal is formed in the respective pixel element. The generating can then be further based upon the at least one transferred quantity of coincidence count signals. A transferred quantity can enter the method in a similar way to a corresponding counted quantity.

The generating unit can be configured for a preprocessing of the data, i.e. a preprocessing of the quantities before an image reconstruction, for a reconstruction of the X-ray image dataset or of a preliminary image dataset based upon the, optionally preprocessed, data and/or for a postprocessing of a reconstructed, preliminary image dataset for generating the final X-ray image dataset. It is, however, also possible that, for example, at least the step of preprocessing is carried out partially or entirely in the context of an "on-board processing" by the X-ray detector or a peripheral electronics unit 61 assigned thereto before a transfer to a generating unit 71, possibly arranged physically separated.

The generating unit 71 can further be configured to output the X-ray image dataset via an interface. The X-ray image dataset can be output, for example, to an output unit 49 in the form of a monitor for a display of the X-ray image dataset for a user or to a storage unit for storage of the X-ray image dataset.

Figure 2:
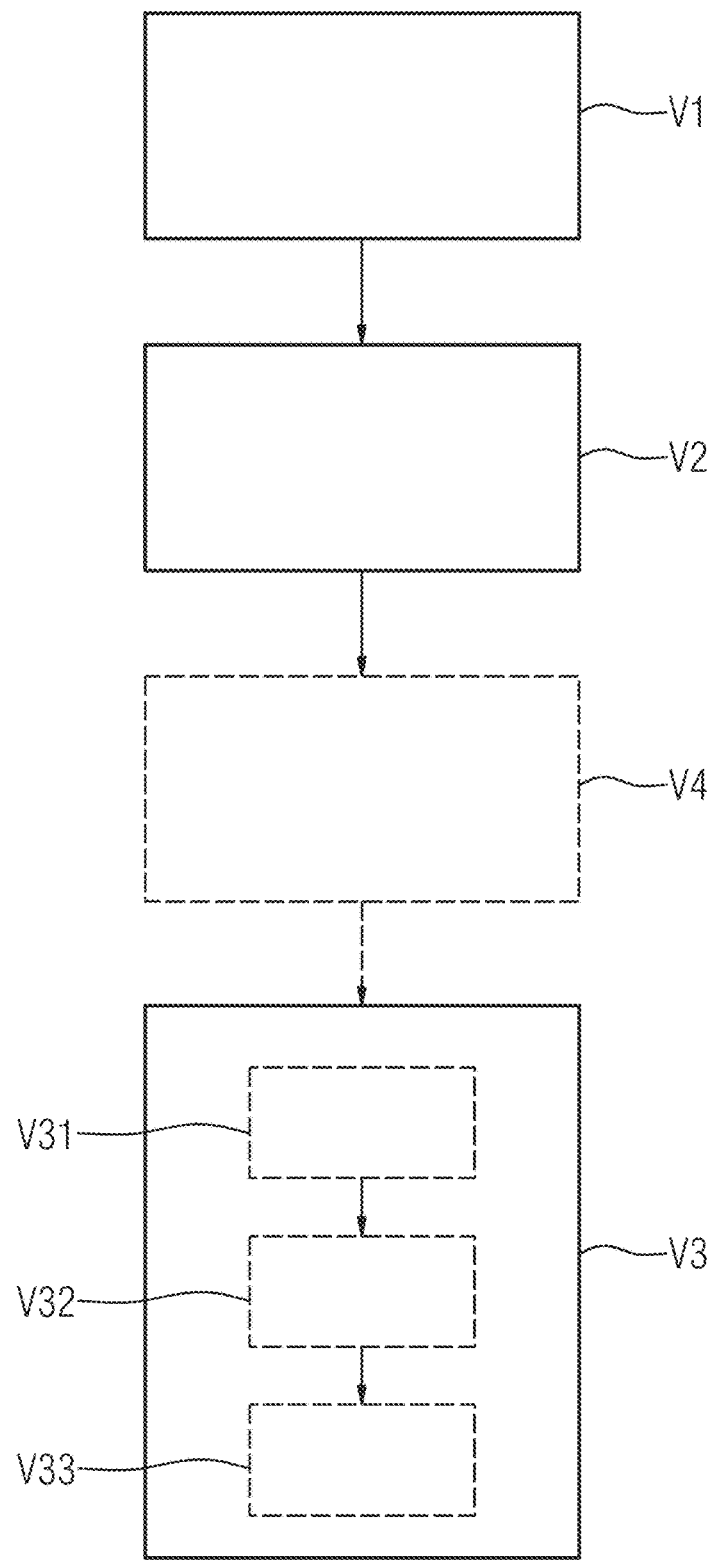
FIG. 2 shows a schematic flow diagram of a method for generating an X-ray image dataset.

FIG. 2 shows a schematic method sequence of a method for generating an X-ray image dataset via an X-ray detector 1 having a converter element 3 which is configured to convert X-ray radiation into an electrical signal, and having a multiplicity of pixel elements 50, each being configured to form a count signal based upon a signal directly entering a pixel element 50 of the multiplicity of pixel elements 50 and wherein at least a subset of the multiplicity of pixel elements 50 is configured to form a coincidence count signal which is based upon a signal directly entering the pixel element 50 of the subset of the multiplicity of pixel elements 50 and upon a coincidentally occurring signal of at least one further pixel element 50 of the multiplicity of pixel elements.

The method comprises the step of the first counting V1 of at least one quantity T of count signals dependent upon the incident X-ray radiation in each pixel element 50 of the multiplicity of pixel elements 50. The method further comprises the step of the second counting V2 of at least one quantity C of coincidence count signals in each pixel element 50 of the subset of the multiplicity of pixel elements 50 which is based upon the signal directly entering the pixel element 50 of the subset of pixel elements 50 and upon a coincidentally occurring signal of at least one further pixel element 50 of the multiplicity of pixel elements 50.

Thereby the quantity T of count signals can be counted during an exposure time window or a readout time window. The exposure time window can thereby correspond to the time window during which the X-ray detector 1 or the respective pixel element 50 of the multiplicity of pixel elements 50 is exposed with X-ray radiation. A readout window can correspond, for example, to the time window between a first readout of the counted quantity and a second readout, following temporally thereafter, of the counted quantities that have been counted since the first readout. The quantity of count signals counted can provide a measure for an intensity of the X-ray radiation that is incident, during the exposure time window or the readout time window, upon the detection volume 60 of the pixel element 50 of the multiplicity of pixel elements 50. Based upon the at least one quantity T of count signals, for example, an X-ray image dataset can be generated to which only the X-ray photons of the X-ray radiation contribute which have been directly incident upon a pixel element 50 (or the detection volume 60 which is assigned to the pixel element 50).

The at least one quantity C of coincidence count signals can be counted, in particular, substantially simultaneously with the at least one quantity T of count signals. The at least one quantity C of coincidence count signals can be counted, in particular, during the same exposure time window or readout window as the at least one quantity T of count signals. Through the counting of the at least one quantity C of coincidence count signals, an X-ray image dataset can be generated in which signals coincidentally occurring, for example, in adjacent pixel elements 50 of the multiplicity of pixel elements 50 can be included in the generating of the X-ray image dataset. Thereby, in particular, disturbance effects on the quantity T of count signals in the pixel elements 50 of the multiplicity of pixel elements 50 can be compensated for or corrected, for example, via fluorescence or charge-sharing. Advantageously, an improved image quality can be achieved thereby. In particular, thereby, a reduced noise level can be achieved, for example, expressed quantitatively, with an improved signal-to-noise ratio (SNR). Depending upon the correction or application of the coincidence information, an improved spatial resolution and/or an improved spectral information item can be enabled.

In the context of the steps of the first counting V1 and/or the second counting V2, in particular, more than one quantity T of count signals and/or more than one quantity C of coincidence count signals in each of the pixel elements 50 of the multiplicity of pixel elements 50 or the subset of the multiplicity of pixel elements 50 can also be ascertained. For example, dependent upon a plurality of energy thresholds S provided in a respective pixel element 50 of the multiplicity of pixel elements 50, a plurality of quantities T of count signals and/or, in a respective pixel element 50 of the subset of pixel elements 50, a plurality of quantities C of coincidence count signals can be counted.

With more than one further pixel element 50 of the multiplicity of pixel elements 50, coincidence count signals can also be formed. Preferably, coincidence count signals can be formed in each pixel element 50 of the subset of the multiplicity of pixel elements 50 with between one and 24 further pixel elements 50 of the multiplicity of pixel elements 50. Preferably, the one to 24 further pixel elements comprise a directly adjacent, a diagonally adjacent pixel element of the multiplicity of pixel elements, or a next but one neighbor of the pixel element of the subset of the multiplicity of pixel elements.

Thereby, the at least one quantity C of coincidence count signals counted in the step of the second counting V2 for each pixel element 50 of the subset of pixel elements 50 can be based upon coincidentally occurring signals of all the further participating pixel elements 50. This means that the at least one quantity of coincidence count signals can represent a sum of the coincidentally occurring signals of the pixel element 50 under consideration of the subset of pixel elements 50 and the one to 24 further involved pixel elements 50 of the multiplicity of pixel elements 50. Alternatively thereto, in the step of the second counting S2, at least one quantity C of coincidence count signals can be counted with each of the one to 24 further pixel elements 50 and therewith a plurality of quantities C of coincidence count signals can be counted, dependent upon the involved pixel elements 50.

The method can also comprise the step of transferring V4, wherein at least one quantity C of coincidence count signals counted in a pixel element 50 of the subset of the multiplicity of pixel elements 50 is transferred to at least one of the further pixel elements 50 with which a coincidence count signal is formed in the respective pixel element 50. The step of generating V3 can then be based upon at least one transferred quantity C of coincidence count signals.

This variant permits, also for pixel elements 50 of the multiplicity of pixel elements 50 which are not part of the subset of the multiplicity of pixel elements 50, quantities of coincidence count signals to be ascertained and coincidence information to be collected which can be used in the method for generating an X-ray image dataset and its variants in a similar manner to a quantity of coincidence count signals counted in the pixel element 50. For example, in a matrix-like arrangement of the multiplicity of pixel elements 50, only every second pixel element 50 of the multiplicity of pixel elements 50 can be part of the subset and thus each be configured to count at least one quantity C of coincidence count signals at least with its four directly adjacent pixel elements 50. For the remainder of the multiplicity of pixel elements 50, the corresponding coincidence information can then be ascertained by a transfer V4. Apart therefrom, other embodiment variants are also possible.

This variant also permits a redundant counting of coincidence count signals in the pixel elements 50 of the subset of the multiplicity of pixel elements 50 to be reduced or the collected coincidence information in a pixel element 50 of the subset of the multiplicity to be extended through a transfer of quantities. For example, each pixel element 50 of the multiplicity counts a quantity C of coincidence count signals, in an example orthogonal pixel grid, with its northern and western directly adjacent and diagonally adjacent north-western and south-western neighboring pixel element 50. The coincidence information of each pixel element 50 to the remaining directly neighboring or diagonally neighboring pixel elements 50 can then be ascertained by way of a transfer of quantities from these pixel elements 50.

A quantity C of coincidence count signals transferred to a pixel element 50 can be utilized in the method for generating an X-ray image dataset and its variants as described in a similar manner as if the corresponding quantity of coincidence count signals had been counted in the pixel element 50 itself.

Preferably, a pixel-specific item of coincidence information underlies a transferred quantity C of coincidence count signals, i.e. the quantity to be transferred is based upon coincidence count signals which are formed only between the pixel element 50 from which the quantity is transferred and the pixel element 50 to which the quantity is transferred. However, variants of the method can exist wherein, if a plurality of further pixel elements 50 is provided for the formation of coincidence count signals, a quantity C of coincidence count signals is transferred which is based upon coincidentally occurring signals of all the further pixel elements 50. Underlying this can be the assumption that at least for pixel elements 50 which are arranged in close proximity and which are therefore subject to similar conditions, also based upon a sum, at least an estimate of a quantity C of coincidence count signals which can be advantageously applied in a method for generating an X-ray image dataset can be possible.

In method variants, in particular for each pixel element 50 of the multiplicity of pixel elements 50, at least a counted or transferred quantity C of coincidence count signals can be ascertained, so that for each pixel element 50 of the multiplicity of pixel elements 50 coincidence information is available.

An advantageous representation of the collected coincidence information of each pixel element 50 in the form of counted and/or transferred quantities C of coincidence count signals can be provided by way of an, at least partially filled, coincidence matrix $\hat{C}$. The counted and/or transferred quantities C of coincidence count signals can then serve as entries of the at least partially filled coincidence matrix $\hat{C}$ of a respective pixel element 50. The coincidence matrix $\hat{C}$ can then represent the collected coincidence information of a pixel element 50 respectively under consideration, dependent upon the at least one, preferably the plurality of further pixel elements 50 of the multiplicity of pixel elements 50 and/or dependent upon the one or more energy thresholds S (based upon which coincidence count signals are formed). The dimensions of such a coincidence matrix $\hat{C}$ and its filling is dependent upon the specific implementation of the signal-carrying circuit arrangement of the pixel elements 50 of the X-ray detector 1 and/or of the possibilities of the transfer of quantities C to at least one further pixel element 50. Such a coincidence matrix $\hat{C}$ is described in greater detail in relation to FIGS. 3 and 4.

The method shown in FIG. 2 for generating an X-ray image dataset comprises, apart from the steps of the first counting V1 and of the second counting V2, the step of generating V3 the X-ray image dataset based upon the at least one quantity T of count signals counted in each pixel element 50 of the multiplicity of pixel elements 50 and the at least one quantity C of coincidence count signals counted in each pixel element 50 of the subset of the multiplicity of pixel elements 50. This can also be based upon a transferred quantity C of coincidence count signals based upon a counted quantity C of coincidence count signals. The coincidence count signals are also included, according to the invention, in the generating V3. If a plurality of quantities T of count signals and/or a plurality of quantities C of coincidence count signals are ascertained, i.e. counted or transferred, a plurality of quantities can also be included accordingly in the generating. Based upon a quantity C of coincidence count signals, for example, the counted quantities T of count signals can be corrected, the quantities C of coincidence count signals can be included as a boundary condition in a reconstruction, as additional image information or otherwise in the generating V3 of the X-ray image dataset.

The generated X-ray image dataset can be, in particular, a three-dimensional image dataset (3D image dataset) or a two-dimensional image dataset (2D image dataset). A 2D image dataset enables a two-dimensional, in particular, a spatially two-dimensional representation. A 3D image dataset enables, in particular, a three-dimensional, in particular, a spatially three-dimensional representation. A three-dimensional image dataset can also be represented as a quantity of slice image datasets, wherein a slice image dataset then enables a two-dimensional, in particular, spatially two-dimensional representation of each layer of the 3D image dataset. A 3D image dataset typically comprises a plurality of voxels, also known as image points. Similarly thereto, a two-dimensional image dataset can also comprise a plurality of (image) pixels, also known as image points. Each image point can have a value, in particular, an image value, for example, a gray value and/or an RGB color value and/or an intensity value. The image values of the voxels or pixels of the generated X-ray image dataset can then be based, in particular, upon the at least one quantity T of count signals counted in the multiplicity of pixel elements 50 and the at least one counted quantity C of coincidence count signals counted in the subset of the multiplicity of pixel elements.

If the method is carried out, for example, via a computed tomography device, the generating can comprise at least the reconstruction of a 3D image dataset or of a 2D image dataset in the form of a slice image dataset via a CT reconstruction algorithm, for example, in the form of a filtered back projection or an iterative CT reconstruction algorithm.

The step of generating V3 can be subdivided into substeps. In the schematic method sequence shown in FIG. 2, it is indicated that the generating V3 can comprise, for example, a substep V31 of the preprocessing of the data before an image reconstruction, a substep V32 of the reconstruction of an X-ray image dataset or of a preliminary image dataset based upon the possibly preprocessed data and a substep of the postprocessing V33 of the reconstructed X-ray image dataset. At least in one of the substeps, the coincidence information counted in the step of the second counting V2 or the coincidence information ascertained in the step of transferring V4 can be included. In particular, in each of the substeps or in a plurality of the substeps, the coincidence information ascertained in the step of the second counting V2 or in the step of the transferring V4, based upon the at least one quantity C of coincidence count signals counted in each pixel element 50 of the subset of pixel elements, can be entered.

The step V31 of the preprocessing can comprise, inter alia, a linearization or a logarithmization of the count information. Corrections can be carried out, for example, a so-called gain correction or an offset correction for equalizing slightly different response behaviors of the pixel elements between one another on irradiation with X-ray radiation or a correction with regard to defective pixel elements. According to one variant of the method, in a step V31 of the preprocessing in each pixel element 50 of the subset of the multiplicity of pixel elements 50, the at least one quantity T of count signals counted can be adapted by way of the at least one quantity C of coincidence count signals.

The step V32 of reconstructing can comprise, inter alia for example, an image reconstruction based upon a filtered back projection or based upon an iterative reconstruction algorithm. An embodiment variant of the method for generating the X-ray image dataset can therein provide that the respective at least one quantity C of coincidence count signals counted or transferred in a pixel element enters an iterative reconstruction algorithm as additional information.

The step V33 of the postprocessing can comprise, inter alia for example, a windowing of the image values of the X-ray image dataset, further corrections, for example, regarding metal artifacts, or a segmentation of structures contained in the X-ray image dataset. In one embodiment variant of the method for generating the X-ray image dataset, the step V3 of generating can comprise that based upon the at least one quantity T of counted count signals in each pixel element 50 of the multiplicity of pixel elements 50, at least a preliminary image dataset is generated, and that based upon the at least one quantity C of coincidence count signals in each pixel element 50 of the subset of pixel elements 50, at least one coincidence image dataset is generated, wherein in the substep V33 of the postprocessing, the at least one coincidence image dataset is applied to the at least one preliminary image dataset. The coincidence image dataset can therein also be based upon a transferred quantity C of coincidence count signals.

Figure 3:
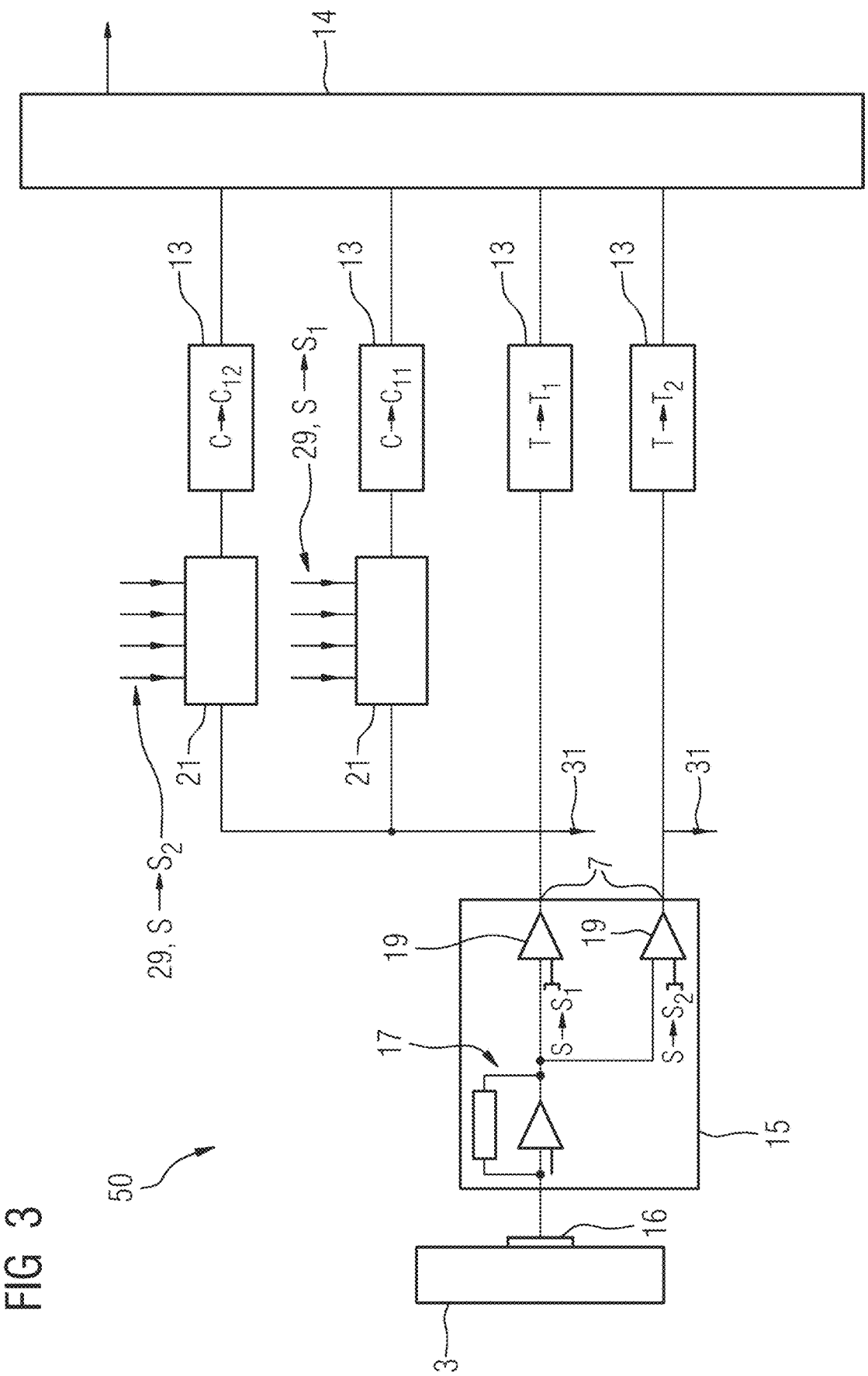
FIGS. 3 and 4 show respective schematic illustrations of an example signal-carrying circuit arrangement of a pixel element of the subset of the multiplicity of pixel elements in different embodiments.
Figure 4:
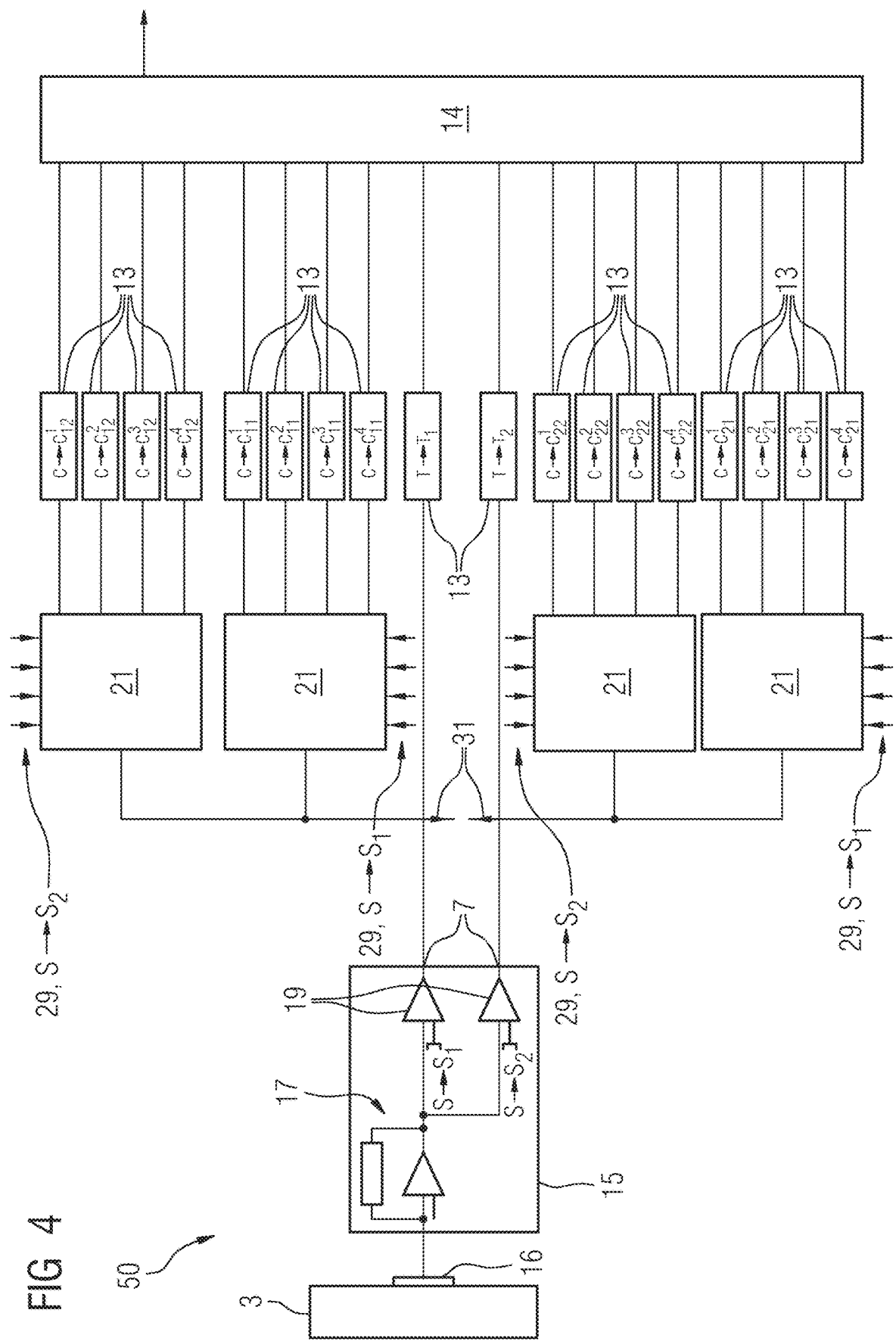

Examples of the entry of the coincidence information into the step of generating are set out more specifically below. FIGS. 3 and 4 each show schematic illustrations of an example signal-carrying circuit arrangement of a pixel element 50 of the subset of pixel elements 50 of an X-ray detector 1 in different embodiments. The examples shown thereby reveal possibilities for a circuit arrangement that can allow a count signal to be formed based upon a signal directly entering the pixel element 50 shown and based thereon, to count at least one quantity T of count signals, and a coincidence count signal to be formed based upon the signal directly entering the pixel element 50 shown and upon a coincidentally occurring signal of at least one further pixel element 50 of the multiplicity of pixel elements 50 and based thereon, to count at least one quantity C of coincidence count signals. The embodiments are selected as examples to illustrate the underlying functional principle. In addition, further circuit arrangements deviating therefrom of the pixel elements 50 are possible within the context of the invention which also permit the counting of a coincidence count signal and the counting of a count signal. Also indicated in the drawings is merely the signal-carrying circuit arrangement of an example pixel element 50 of the subset of pixel elements 50, and merely in a severely abstracted form, with the components necessary for illustration. The circuit arrangement can also, however, easily be transferred to the other pixel elements 50 of the at least subset of pixel elements 50. Additionally, further processing components can also be provided in a pixel element 50, i.e. in the pixel-specific pixel electronics unit of a pixel element 50.

In FIG. 3, the pixel element 50 of the subset of pixel elements 50 shown by way of example has a converting apparatus 15 with at least one signal amplifier 17 and a quantity of, in this case for example two, comparators 19. The signal input of the converting apparatus 15, in particular of the signal amplifier 17, is coupled in a signal-carrying manner to the associated sensitive detection volume in the converter element 3 via the sensor pixel electrode 16. The signal amplifier 17 amplifies the electrical signal directly entering the pixel element 50 via the sensor pixel electrode 16 and generated by incident X-ray radiation via the converter element 3 for the subsequent further processing.

The comparators 19 of the pixel element 50 shown each have an adjustable energy threshold S. The adjustable energy thresholds S of different comparators 19 can be adjusted to different energy threshold values. This is illustrated in the drawing by the indication $S \rightarrow S_1$ and $S \rightarrow S_2$, with which it is essentially to be expressed that the comparators have two differently adjusted energy thresholds $S \rightarrow S_1$ and $S \rightarrow S_2$ with different energy threshold values. In the following, a first energy threshold $S \rightarrow S_1$ and a second energy threshold $S \rightarrow S_2$ of the pixel element 50 can be referred to. For example, the energy threshold $S \rightarrow S_1$ has, in relation to the energy of the incident X-ray radiation, a lower energy threshold value than the energy threshold $S \rightarrow S_2$. Typically, the energy thresholds S of different pixel elements 50 of the multiplicity of pixel elements 50 are each adjusted to the same energy threshold values. However, other embodiments can also exist.

Via the comparators 19, the signal directly entering the pixel element 50 under consideration via the sensor pixel electrode 16 is compared with the respective energy thresholds $S \rightarrow S_1$ and $S \rightarrow S_2$ of the comparators 19. When a corresponding energy threshold S is exceeded, an output signal which serves as a count signal is formed at the signal output 7 of the comparator 19, the energy threshold of which S has been exceeded. If both the energy thresholds $S \rightarrow S_1$ and $S \rightarrow S_2$ are exceeded, a count signal is respectively formed at both the signal outputs 7 of the comparators 19.

According to one embodiment of the X-ray detector 1, in each pixel element 50 of the subset of pixel elements 50, based upon the output signal at the signal output 7, at least one comparator 19 of the quantity of comparators of the respective pixel element 50, the at least one quantity T of count signals and, based upon the output signal 7 of at least one comparator 19 of the quantity of comparators of the respective pixel element 50 of the subset of pixel elements 50 and at least upon the output signal 7 of a comparator 19 of the quantity of comparators of the at least one further pixel element 50 of the multiplicity of pixel elements 50, the at least one quantity C of coincidence count signals is counted. In general, in a pixel element 50 of the subset, the comparators 19 upon which the at least one quantity T of count signals is based can be different from the comparator 19 of the quantity of comparators upon which the at least one quantity C of coincidence count signals is based. However, it can also be the same comparator 19, as in this example.

In the example shown in FIG. 3, the signal outputs 7 of the comparators 19 are each linked in a signal-carrying manner to a counting element 13. A respective counting element 13 is configured to count a quantity T of count signals, based upon the output signal of each linked comparator 19. In the case shown, based upon the output signals of the two comparators 19, a quantity T of count signals is counted in each case. This means, in the case shown, that one of the counting elements 13 counts a quantity $T \rightarrow T_1$ of count signals dependent upon the energy threshold $S \rightarrow S_1$ and a further counting element 13 counts a quantity $T \rightarrow T_2$ of count signals dependent upon the energy threshold $S \rightarrow S_2$.

In the case shown in FIG. 3, the comparator 19 having the energy threshold $S \rightarrow S_1$ is also linked in a signal-carrying manner to two coincidence logic units 21. In other embodiments, only one or further coincidence logic units 21 can be provided. It is preferably provided that the signal output 7 of at least one of the comparators 19 of the quantity of comparators 19 of a pixel element 50 of the subset of pixel elements 50 is linked in a signal-carrying manner to at least one coincidence logic unit 21. Based upon the output signal of the respective coincidence logic unit 21, via a further counting element 13 linked to the respective coincidence logic unit 21, a quantity C of coincidence count signals can be counted.

A respective coincidence logic unit 21 is configured to form a coincidence count signal which is based upon the signal directly entering the pixel element 50 of the subset of pixel elements 50, and upon a coincidentally occurring signal of at least one further pixel element 50 of the multiplicity of pixel elements. A respective coincidence logic unit 21 is also linked for this purpose to at least one further pixel element 50 of the multiplicity of pixel elements via at least one further signal input 29 of the coincidence logic unit 21.

In particular, a respective coincidence logic unit 21 is configured according to a preferred embodiment, based upon the output signal 7 of the at least one comparator 19 of the pixel element under consideration 50, said comparator being coupled to the coincidence logic unit 21, and based at least upon the output signal of a comparator 19 of at least one further pixel element 50 (not shown here), to form a coincidence count signal and to provide it at a signal output of the coincidence logic unit 21. This means that in this embodiment, a respective signal input 29 of the coincidence logic unit 21 is coupled, in each case, in a signal-carrying manner to a comparator 19 of the quantity of comparators of a further pixel element 50 of the multiplicity of pixel elements 50. In the specific example of FIG. 3, a respective coincidence logic unit 21 is linked, by way of example, to four further pixel elements 50 of the multiplicity of pixel elements in a signal-carrying manner. For this purpose, a respective coincidence logic unit 21 has four signal inputs 29 each of which is coupled to a further pixel element 50 of the multiplicity of pixel elements 50 in a signal-carrying manner.

In the case shown, the lower of the coincidence logic units 21 is linked to a comparator 19 of the quantity of comparators of the respective further pixel element 50 which has the energy threshold $S \rightarrow S_1$ (indicated in FIG. 3 by the indication $S \rightarrow S_1$ in relation to the signal outputs 29 of the lower coincidence logic unit 21 in the drawing). Accordingly, the quantity C of coincidence count signals counted by the counting element 13 linked to this coincidence logic unit 21 corresponds to the quantity of coincidentally occurring signals which have exceeded the energy threshold $S \rightarrow S_1$ in the pixel element 50 under consideration and at least in one of the further pixel elements 50 linked to the coincidence logic unit 21. In other words, in this case, a quantity $C \rightarrow C_{11}$ of coincidence count signals of the energy threshold $S \rightarrow S_1$ of the pixel element 50 under consideration is counted with the energy threshold $S \rightarrow S_1$ of at least one of the further pixel elements 50 of the multiplicity of pixel elements 50.

Proceeding from the assumption that the energy threshold $S \rightarrow S_1$ in each pixel element 50 of the multiplicity of pixel elements 50 is adjusted to the same energy threshold, according to a preferred variant, the adjustable energy threshold S of the at least one comparator 19 of the quantity of comparators of the pixel element 50 under consideration of the subset of pixel elements 50 and the adjustable energy threshold S of the at least one comparator 19 of the quantity of comparators of at the at least one further pixel element 50 of the multiplicity of pixel elements 50 (in the example shown, the four further pixel elements 50 in each case) has the same energy threshold value. This means, in this case, a quantity $C \rightarrow C_{11}$ of coincidence counter signals is counted based upon the same energy threshold $S \rightarrow S_1$ of the respectively involved pixel elements 50 of the multiplicity of pixel elements 50. This can also be denoted an (energy-)symmetrical exceeding of energy thresholds or an (energy-) symmetrical coincidence.

In the case shown in FIG. 3, the upper of the coincidence logic units 21 is also linked via a signal input 29 to a comparator 19 of the quantity of comparators of the respective further pixel element 50 which has the energy threshold $S \rightarrow S_2$ (indicated in FIG. 3 by the indication $S \rightarrow S_2$ in relation to the signal outputs 29 of the upper coincidence logic unit 21 in the drawing). In other words, in this case, a quantity $C \rightarrow C_{12}$ of coincidence count signals of the energy threshold $S \rightarrow S_1$ of the pixel element 50 under consideration of the subset of pixel elements 50 is counted with the energy threshold $S \rightarrow S_2$ of the at least one further pixel element 50 of the multiplicity of pixel elements (in this example, the four further pixel elements 50). Accordingly, a counted quantity $C \rightarrow C_{12}$ of coincidence count signals based upon the output signal of this coincidence logic unit 21 corresponds to the quantity of coincidentally occurring signals which have exceeded the energy threshold $S \rightarrow S_1$ in the pixel element 50 under consideration of the multiplicity of pixel elements 50 and have exceeded the energy threshold $S \rightarrow S_2$ in at least one of the further linked pixel elements 50.

Proceeding from the assumption that the energy threshold $S \rightarrow S_1$ of the pixel element under consideration and the energy threshold $S \rightarrow S_2$ of the at least one further pixel element 50 of the multiplicity of pixel elements 50 are adjusted to different energy threshold values, this means that for the second counting V2 of the at least one quantity C of coincidence count signals, the adjustable energy threshold S of the at least one comparator 19 of the quantity of comparators of the respective pixel element 50 of the subset of pixel elements 50 and the adjustable energy threshold S of the at least one comparator 19 of the quantity of comparators of the at least one further pixel element 50 of the multiplicity of pixel elements 50, on which the coincidence count signal is based, have different energy threshold values. This means, in this case, a quantity $C \rightarrow C_{12}$ of coincidence counter signals is counted based upon the different energy thresholds $S \rightarrow S_1$ and $S \rightarrow S_2$ of the respectively involved pixel elements 50 of the multiplicity of pixel elements 50. This can also be denoted an (energy-)asymmetrical exceeding of energy thresholds S.

Furthermore, in the example shown in FIG. 3, coupled to each of the comparators 19, an output 31 is provided, by which a corresponding output signal can be output at one or a plurality of further pixel elements 50 of the subset of pixel elements 50 in order to serve equally as an input signal of a coincidence logic unit 21 of one of the further pixel elements (not shown here) of the subset of pixel elements 50.

The quantities T→$T_1$ and T→$T_2$ of count signals and the quantities C→$C_{11}$ and C→$C_{12}$ of coincidence count signals can then be read out from the counting elements 13 via a readout element 14 and output together with the counted quantities of the multiplicity of pixel elements 50 of the X-ray detector 1, possibly already preprocessed, for example, at a generating unit 71 for the generating V3 of the X-ray image dataset, based upon the quantities. Advantageously, counted quantities T of count signals and counted quantities C of coincidence count signals can be provided for the generating of the X-ray image dataset.

In the example shown, a coincidence logic unit 21 is linked, by way of example, to four further pixel elements 50 of the multiplicity of pixel elements 50 in a signal-carrying manner via the signal inputs 29. This means that coincidence count signals are formed based upon coincidentally occurring signals from four further pixel elements 50 of the multiplicity of pixel elements 50. For example, the four further pixel elements 50 in FIG. 3 can comprise the four directly adjacent pixel elements 50 of the pixel element 50 under consideration in a matrix-like arrangement of the multiplicity of pixel elements 50. The pixel elements 50 directly adjacent to a pixel element 50 under consideration can comprise, in particular, the pixel elements 50 of the multiplicity of pixel elements each having a common edge in a pixel grid defined by the matrix-like arrangement of the multiplicity of pixel elements 50. However, another selection and/or quantity of further pixel elements 50 can also be provided. For example, alternatively or additionally, coincidence count signals can be formed based upon diagonally adjacent pixel elements 50. For example, next but one neighbors, i.e. pixel elements adjacent to the pixel elements directly adjacent to the pixel element under observation, can be observed regarding coincidentally occurring signals. Advantageously, at least with these further pixel elements 50, coincidence count signals are formed in which coincidental signals occur with a high probability. In preferred embodiment variants, in particular, coincidence count signals can be formed in each pixel element 50 of the subset of pixel elements 50 with between one and 24 further pixel elements 50 of the multiplicity of pixel elements 50.

The quantity and selection of further pixel elements 50 upon which the coincidence count signal is based can also vary within the subset of the multiplicity of pixel elements 50. For example, for pixel elements 50 arranged at the edge in a matrix-like arrangement of the multiplicity of pixel elements 50, a different quantity and selection of further pixel elements 50 can be taken into account regarding coincidentally occurring signals than pixel elements 50 arranged centrally in a matrix-like arrangement of the multiplicity of pixel elements 50. Thus, for example, pixel elements arranged at the edge have only three directly adjacent pixel elements.

In other embodiment variants, it can be provided that, alternatively or additionally, a quantity C→$C_{22}$ and/or a quantity C→$C_{21}$ based upon the energy threshold S→$S_2$ of the pixel element 50 under consideration and corresponding output signals of the comparators of the further linked pixel elements 50 of the multiplicity of pixel elements 50 is counted. Accordingly, in the example shown in FIG. 3, alternatively or additionally, at least one further coincidence logic unit 21 can be provided, which is coupled to the comparator 19 having the energy threshold S→$S_2$ of the pixel element 50 under consideration. Similarly, it can be provided in embodiments that only one quantity C of coincidence count signals, for example, a quantity C→$C_{11}$ is counted. Furthermore, it can be provided in alternative embodiment variants that only one comparator 19 or more than two comparators 19, each with an adjustable energy threshold S for forming count signals or coincidence count signals, are made available.

In the context of the invention, dependent upon the circuit arrangement of the pixel element 50 under consideration of the subset of pixel elements 50, at least one quantity C→$C_{nm}$ of coincidence count signals is counted in the pixel element 50 under consideration, wherein n∈{1, . . . , N} with the number N of energy thresholds S→$S_n$ provided in the pixel element 50 under consideration and wherein m∈{1, . . . , M} with the number M of energy thresholds S→$S_m$ provided of the at least one further pixel element 50 of the multiplicity of pixel elements upon which the coincidence count signals are based. Preferably, a plurality of quantities C→$C_{nm}$ of coincidence count signals are counted in each pixel element 50 of the subset of pixel elements 50. Advantageously, a plurality of counted quantities of coincidence count signals permits a further-reaching, improved correction of the X-ray image dataset. In particular, when taking account both of symmetrical and also asymmetrical exceedings, an improved spatial resolution can also be achieved in an improved manner.

It can also be provided that in a respective pixel element 50 of the subset of pixel elements, apart from comparators provided for counting count signals, one or a plurality of separate comparators are each provided for counting coincidence count signals 19, based upon which only coincidence count signals are counted.

If apart from pixel elements 50 which are part of the subset of the multiplicity of pixel elements 50, pixel elements 50 are also provided which are configured only for counting count signals, these can each have, in particular, at least one signal amplifier 17, a quantity of comparators 19 coupled thereto and a counting element 13 connected in a signal-carrying manner to a signal output 7 of a comparator 19 of the quantity of comparators 19. The output signal of at least one comparator 19 can possibly also be fed into a pixel element 50 of the subset of the multiplicity, on the basis of which in the pixel element 50 of the subset of the multiplicity of pixel elements 50, a coincidence count signal can be formed.

In the example shown in FIG. 3, on counting the quantities C of coincidence count signals, no distinction is made between the individual further linked pixel elements 50 of the multiplicity of pixel elements 50. This means that, in this example, the at least one quantity C of coincidence count signals counted in the step of the second counting V2 for each pixel element 50 of the subset of the multiplicity of pixel elements 50 is based upon coincidentally occurring signals of all the further participating pixel elements 50. In other words, in the example shown, the respectively counted quantity C of coincidence count signals in a respective counting element 13 is incremented by one count unit if a coincidentally occurring signal arises in at least one of the further linked pixel elements 50. In other words, the counted at least one quantity C of coincidence count signals in the example shown represents a sum of coincidentally occurring signals in all the further linked pixel elements 50. In other embodiments, it can be provided, however, that for each of the further linked pixel elements 50, a quantity C of coincidence count signals is counted. This means that in the step of the second counting V2, it can be provided that at least one quantity C of coincidence count signals is counted with each of the further pixel elements 50.

FIG. 4 illustrates an example circuit arrangement of a pixel element 50 for counting count signals or coincidence count signals, wherein in this case, apart from a quantity T→$T_1$ of count signals based upon an energy threshold S→$S_1$ and a quantity T→$T_2$ of count signals based upon an energy threshold S→$S_2$ of the pixel element 50 under consideration for each of the, in the example shown four, further linked pixel elements 50 (index i=1, . . . , 4) quantities C→$C_{nm}^i$ of coincidence count signals are counted, based upon the energy thresholds S→$S_n$ where n=1,2, of the pixel element 50 under consideration and the energy thresholds S→$S_m$ of the respectively linked further pixel element 50 with the index i where m=1,2. Similarly to the example in FIG. 3, the quantity C→$C_{nm}^i$ of coincidence count signals accordingly reproduces the quantity of coincidentally occurring signals which have exceeded the energy threshold S→$S_n$ in the pixel element 50 under consideration and the energy threshold S→$S_m$ in the further pixel element 50 with the index i.

The transfer to another quantity of comparators 19 provided, each having respectively adjustable energy thresholds S and a different number of further linked pixel elements 50, is herein easily possible.

It can also be provided in the circuit arrangement of the pixel elements 50 that a redundant elicitation of coincidence count signals is prevented. Underlying this is the consideration that coincidences occur (pixel-)symmetrically. It can thus, for example, be expected that a quantity C of coincidence count signals which are elicited between a pixel element 50 with the index p and a pixel element 50 with the index i is equal to the corresponding quantity C of coincidence count signals which has been counted in the pixel element 50 with the index i with the pixel element p. For example, it can be assumed that a quantity C→$^pC_{11}^i$ of coincidence count signals is equal to a quantity C→$^iC_{11}^p$ of coincidence count signals. For example, it can be assumed that a quantity C→$^pC_{12}^i$ of coincidence count signals is equal to a quantity C→$^iC_{21}^p$ of coincidence count signals. For the completion of the coincidence information in a respective pixel element, a transfer of quantities of coincidence count signals between the pixel elements can then be provided. In this way, a simplified circuit arrangement can be provided at least partially.

An advantageous representation of the counted or transferred quantities C of coincidence count signals in a pixel element 50 can be provided via a coincidence matrix $\hat{C}$ which describes the respective counted quantity or the counted and/or transferred counts C of coincidence count signals of a pixel element 50.

Proceeding from the assumption that, as shown in the example in FIG. 4, for each further pixel element 50 with the index i linked to the pixel element 50 under consideration, quantities C of coincidence count signals are counted or possibly also transferred, i.e. a pixel-specific item of coincidence information is available, for a pixel element 50 under consideration, a three-dimensional coincidence matrix $\hat{C}$ can be created, wherein $$\hat{C}(:,:,i) = \hat{C}_i = \begin{bmatrix} c_{11}^i & c_{12}^i & \ldots & c_{1M}^i \\ c_{21}^i & c_{22}^i & \ldots & c_{2M}^i \\ \vdots & \vdots & \ddots & \vdots \\ c_{N1}^i & c_{N2}^i & \ldots & c_{NM}^i \end{bmatrix}$$

where i=1, . . . , I and I=quantity of further pixel elements 50 linked to the pixel element 50 under consideration, on the basis of which quantities of coincidence count signals are ascertained and N=quantity of the energy thresholds S in the pixel element 50 under consideration of the multiplicity of pixel elements 50 or M=quantity of the energy thresholds S in the further pixel element with the index i, based upon which quantities C of coincidence count signals are ascertained.

According to the above description, the quantity C→$C_{11}^i$ of coincidence count signals corresponds to the coincidences of the energy threshold S→$S_1$ of the pixel element 50 under consideration with the energy threshold S→$S_1$ of the further pixel element with the index i, the quantity C→$C_{12}^i$ of coincidence count signals corresponds to the coincidences of the energy threshold S→$S_1$ of the pixel element 50 under consideration with the energy threshold S→$S_2$ of the further pixel element with the index i, the quantity C→$C_{22}^i$ of coincidence count signals corresponds to the coincidences of the energy threshold S→$S_2$ of the pixel element under consideration with the energy threshold S→$S_2$ of the further pixel element with the index i, etc.

The dimension of the coincidence matrix $\hat{C}$ depends upon the configuration and circuit arrangement of the pixel elements 50. Similarly, according to the configuration and circuit arrangement, the coincidence matrix $\hat{C}$ can be filled only partially with entries based upon counted or transferred quantities of coincidence count signals.

In relation to the specific example of a signal-carrying circuit arrangement in FIG. 4, for example, there results a three-dimensional coincidence matrix $\hat{C}$ with the dimensions 2×2×4, wherein $$\hat{C}(:,:,i) = \hat{C}_i = \begin{bmatrix} c_{11}^i & c_{12}^i \\ c_{21}^i & c_{22}^i \end{bmatrix}$$

where i=1, . . . , 4.

If, when counting the coincidence count signals, no distinction is made between the linked further pixel elements 50, the coincidence matrix $\hat{C}$ of a pixel element 50 can be represented by a two-dimensional matrix:

$$\hat{C} = \begin{bmatrix} C_{11} & C_{12} & \ldots & C_{1M} \\ C_{21} & C_{22} & \ldots & C_{2M} \\ \vdots & \vdots & \ddots & \vdots \\ C_{N1} & C_{N2} & \ldots & C_{NM} \end{bmatrix}$$

wherein the individual entries $C_{nm}$ are each based upon coincidentally occurring signals of all the further linked pixel elements 50, i.e. corresponding to the sum of coincidentally occurring signals in all the further linked pixel elements 50.

In the specific example shown in FIG. 3, this two-dimensional matrix $\hat{C}$ is reduced for the pixel element 50 under consideration to:

$$\hat{C} = [C_{11} C_{12}]$$

Equally, from a three-dimensional coincidence matrix $\hat{C}$, a two-dimensional coincidence matrix $\hat{C}$ can be determined, provided this is advantageous for a further processing of the coincidence information, wherein the entries of the two-dimensional coincidence matrix $\hat{C}$ can then each be determined from the sum $$C_{nm} = \sum_i C_{nm}^i.$$

As previously described in the context of FIG. 2, the coincidence information ascertained can be introduced in different ways into the generating V3 of the X-ray image dataset. Thereby, even a coincidence information item summed across the further pixel elements 50, representable by a two-dimensional coincidence matrix, can be sufficient for the provision of an improved image quality of the X-ray image dataset. Thus, the quantity of coincidences of a pixel element with any neighbors can already convey a large part of the information. However, the provision of a more detailed coincidence information item, representable by a three-dimensional coincidence matrix, permits a particularly versatile use and, in particular, with the inclusion of more detailed directional information, better possibilities for achieving an improved spatial resolution, wherein a less detailed coincidence information item usually implies a smaller circuit design effort.

In the following, in relation to the method for generating an X-ray image dataset in FIG. 2, specific example embodiments (in the following, variants 1 to 5), it is to be demonstrated how ascertained coincidence information can enter into the step of the generating V3 of the X-ray image dataset.

For the further illustration, it is assumed that with the aid of a suitable signal-carrying circuit arrangement of the respective pixel elements 50 of the multiplicity of pixel elements 50, the respective coincidence information items necessary for the respective variants described by way of example for the pixel elements 50 of the multiplicity of pixel elements can be ascertained by counting or transferring.

Similarly, for the following illustrations, it is assumed that an energy threshold denoted with S→S$_1$ assumes a lower energy threshold value than an energy threshold denoted with S→S$_2$. Furthermore, for the following illustration, it is assumed that each of the pixel elements 50 of the multiplicity of pixel elements 50 has energy thresholds S, each having the same energy threshold value.

These example conditions serve merely for easier illustration and better intelligibility of the variants described. Proceeding therefrom, further embodiment variants are derivable, which are also more complex. In addition, any combinations of the variants described here are possible.

Preferably, one or a plurality of quantities C of coincidence count signals, at least with the four directly adjacent pixel elements 50, are ascertained below. More preferably, quantities C of coincidence count signals are ascertained at least with the four directly adjacent and the diagonally adjacent pixel elements 50.

Variant 1:

According to one variant embodiment of the method, in a step V31 of the preprocessing in each pixel element 50 of the subset of the multiplicity of pixel elements 50, the at least one counted quantity T of count signals is adapted by way of the at least one quantity C of coincidence count signals. For example, in the substep V31 of the preprocessing, at least in each pixel element 50 of the subset of pixel elements 50, the at least one quantity C of coincidence count signals is subtracted from the at least one quantity T of counted count signals or is added to the at least one quantity T of counted count signals. This can also comprise a weighted addition or subtraction. The subtraction or addition can thus comprise a factor so that just a portion or a multiple of the at least one quantity C of coincidence count signals is subtracted or added. Equally, at least one quantity C of coincidence count signals transferred to a pixel element 50 of the multiplicity of pixel elements 50 can be subtracted from a quantity of count signals counted in the pixel element 50 or added to the at least one quantity of count signals. If, in a respective pixel element 50 of the multiplicity of pixel elements 50, a plurality of quantities T of count signals and/or a plurality of quantities C of coincidence count signals are ascertained, for example, at least one of the quantities C of coincidence count signals can be added to or subtracted from at least one of the quantities T of count signals.

A particularly simple embodiment of this variant can thereby provide that in each pixel element 50 of the multiplicity of pixel elements 50, a portion of a quantity C→C$_{11}$ of coincidence count signals is subtracted from a quantity T→T$_1$ of count signals, dependent upon an energy threshold S→S$_1$. Therein, the quantity C→C$_{11}$ of coincidence count signals can correspond, in particular, to the sum of all the linked further I pixel elements 50. It is therein assumed that coincidentally occurring signals which have exceeded the energy threshold S→S$_1$ both in the pixel element 50 under consideration of the multiplicity of pixel elements 50 and also in at least one of the further linked pixel element 50 are to be assigned only partially to the pixel element under consideration. For example, it can be assumed that only half of the coincidentally occurring signals are to be assigned to the respective pixel element itself, so that a corrected quantity T'$_1$ of count signals in each pixel element 50 of the multiplicity of pixel elements 50 can be given by:

$$T'_1 = T_1 - \frac{1}{2} * C_{11}$$

Apart from the factor $$\frac{1}{2},$$

another factor can also be applied with other assumptions.

Thereby, the quantity T→T$_1$ of count signals can already be preprocessed. For example, the correction to already linearized or logarithmized data can take place.

In a further embodiment of this variant, the quantity C→C$_{11}$ of coincidence count signals can also be used to correct a quantity T→T$_2$ of count signals based upon a second energy threshold S→S$_2$. For example, the quantity T→T$_2$ of count signals can also be adapted through addition or subtraction of a portion of a quantity C→C$_{11}$ of coincidence count signals. It can thereby be assumed that at least one portion of the coincidentally occurring signals that have exceeded the energy threshold S→S$_1$ both in the pixel element 50 under consideration and also in at least one further pixel element 50, if there had been no allocation of the signal to at least two pixel elements 50, would actually be attributable to a higher energy threshold S. A corrected quantity T'$_2$ of count signals in a pixel element 50 can be given, for example, by $$T'_2 = T_2 + a * C_{11}$$

The parameter a can be specified, for example, empirically or by way of simulation. The parameter a can, in particular, depend upon and be specified by the energy spectrum of the incident X-ray radiation and/or on the energy threshold value of the adjustable energy thresholds.

In a further embodiment of this variant, it can be provided that in each pixel element 50, the at least one portion of a quantity $C \rightarrow C_{12}$ of coincidence count signals is subtracted from a quantity $T \rightarrow T_1$ of count signals, dependent upon an energy threshold $S \rightarrow S_1$. This means that in this case, specifically those instances in which, in the respective pixel element 50, only the energy threshold $S \rightarrow S_1$, while in a further pixel element 50, the energy threshold $S \rightarrow S_2$ has been exceeded, are subtracted from the quantity $T \rightarrow T_1$ based upon the energy threshold $S \rightarrow S_1$. This can be evaluated as an indication that in the further pixel element, the majority of the energy of an incident X-ray photon has been deposited and thus the strike has, with a high probability, taken place in the further pixel element 50 and not in the pixel element 50 under consideration. A corrected quantity $T'_1$ of count signals in a pixel element 50 can then be given, for example, by:

$$T'_1 = T_1 - b * C_{12}$$

The parameter b can be selected, for example in a simplest variant, as b=1. However, it can also be selected differently. The parameter b can be specified, for example, empirically or by way of simulations.

In a further embodiment of this variant, it can be provided that both a quantity $C \rightarrow C_{11}$ and also a quantity $C \rightarrow C_{12}$ of coincidence count signals are used for a correction of the quantity $T \rightarrow T_1$. Through a combination of the embodiments described above, for example, a corrected quantity of count signals in a pixel element 50 can be given by:

$$T'_1 = T_1 - C_{12} - 0.5 * (C_{11} - C_{12}) = T_1 - 0.5 * (C_{11} + C_{12})$$

wherein a doubled subtraction of the quantity $C \rightarrow C_{12}$ of coincidence count signals is avoided.

In the last two cases, therefore, in particular at least one quantity C of coincidence count signals is used, wherein the adjustable energy threshold S of the at least one comparator 19 of the quantity of comparators of the respective pixel element 50 and the adjustable energy threshold S of the at least one comparator 19 of the quantity of comparators of the at least one further pixel element 50 of the multiplicity of pixel elements 50, upon which the coincidence count signals are based, have different energy threshold values. This means the coincidence count signals based upon an asymmetrical exceeding of the energy thresholds S. In other words, at least one quantity C of coincidence count signals based upon different energy thresholds S is used. These quantities correspond, in particular, to the minor diagonal entries of a previously described coincidence matrix $\hat{C}$. In the latter case, in particular, both at least one quantity C of coincidence count signals based upon different energy thresholds S and also at least one quantity C of coincidence count signals based upon the same energy thresholds S is used. It advantageously results therefrom that additionally or alternatively to a correction of the noise increase, for at least one portion of the coincidences, an assignment of double counts to the correct pixel element can also be achieved at least partially. Without the coincidence count signals based upon an asymmetrical exceeding of the energy thresholds S, i.e. the minor diagonal entries of the coincidence matrix $\hat{C}$, such a correction would not be possible.

Apart from the specific examples for a correction of the quantities $T \rightarrow T_1$ and $T \rightarrow T_2$ of count signals set out here based upon the energy threshold $S \rightarrow S_1$ or $S \rightarrow S_2$, further quantities T based upon further energy thresholds S can also be corrected in a transferrable manner. Advantageously, an improved X-ray image dataset can be generated based upon the coincidence information.

Variant 2:

A further embodiment variant of the method for generating the X-ray image dataset provides that the step of generating V3 comprises the use of a trained function, wherein the at least one quantity C of coincidence count signals in at least one pixel element 50 of the subset of pixel elements 50 enters into the trained function as an input parameter. Based thereon, in the step of preprocessing V31, for example, a correction of the at least one quantity T of count signals can be carried out, which also takes account of more complex relationships between the at least one quantity C of coincidence count signals and the at least one quantity T of count signals and/or also further influence variables on the counted quantities. Further influence variables can comprise, for example, temperature effects or time-dependent or radiation-dependent drift effects or the like. If a plurality of quantities C of coincidence count signals are ascertained in a respective pixel element 50, accordingly, the plurality of quantities C of coincidence count signals can be entered as input parameters into the trained function.

Variant 3:

A further embodiment variant of the method for generating the X-ray image dataset provides that the at least one quantity C of coincidence count signals enters an iterative reconstruction algorithm. The coincidence information can be used in the iterative reconstruction in order to achieve an improved image quality, for example, a reduced noise. For example, the coincidence information can be used in the forward projection in a model-based iterative reconstruction. Furthermore, an improved spatial resolution can be achieved in that, in particular, a pixel-specific coincidence information item, i.e. a differentiation of the pixel elements involved in a coincidence signal is used. By this means, a directional information item of the coincidences can be included. In this way, for example, in the context of the reconstruction, a transfer of the collected information to a finer subpixel grid, similar to the variant 5 described below can be enabled, which can be used in the context of the iterative reconstruction.

Variant 4:

A further embodiment variant of the method for generating the X-ray image dataset provides that the step V3 of generating includes that, based upon the at least one quantity T of count signals counted in the pixel elements 50, at least one preliminary image dataset is generated, and that based upon the at least one quantity C of coincidence count signals counted in the pixel elements 50 of the subset of the multiplicity of pixel elements 50, at least one coincidence image dataset is generated. In a substep V33 of the post-processing, the at least one coincidence image dataset can be applied to the at least one preliminary image dataset. In this case, the degradation of the image quality due to coincidences occurring can be reduced by correction on the basis of reconstructed image data rather than corrections based upon scanned raw data, i.e. the quantities T of count signals. In a simple form, the application of the at least one coincidence image dataset can comprise a simple linear combination of the reconstructed image datasets, i.e. of the coincidence image dataset and of the preliminary X-ray image dataset. It can also comprise a weighted linear combination. Similarly for example, a combination of the at least one coincidence image dataset and of the at least one preliminary image dataset is possible based upon a polynomial function or another application.

If a plurality of quantities C of coincidence count signals are ascertained in the pixel elements 50, a plurality of coincidence image datasets can also be generated, which can be applied to one or a plurality of preliminary image datasets, based upon count signals counted in each pixel element 50 of the multiplicity of pixel elements. If the coincidence information is available representable by a three-dimensional or a two-dimensional coincidence matrix C, the complete tensor $\hat{C}$, as well as individual components such as submatrices $\hat{C}_i$ or respective entries $C_{nm}{}^i$ or $C_{nm}$ can be processed to coincidence image data which can be applied in a step of the postprocessing for improving the image quality of the X-ray image dataset to a preliminary image dataset. Here also, for example, a markedly improved spatial resolution can be achieved in that a pixel-specific coincidence information item is used to achieve a transfer to a finer voxel or pixel grid based upon the reconstructed image data similarly to variant 5 as described below, i.e. to transfer the image values of the voxels or image pixels calculated from the quantities of count signals and quantities of coincidence count signals to newer (smaller) voxels or image pixels.

Variant 5

A further embodiment variant of the method for generating the X-ray image dataset provides for the scanned coincidence information to be used to transfer the scan data of the pixel elements in a better manner to a finer subpixel grid. Thereby, advantageously, an improved spatial resolution in the X-ray image dataset can be enabled. In this variant of the method, it is assumed that, in particular, a pixel-specific coincidence information item is available, i.e. that for each of the further pixel elements 50 linked for the formation of the coincidence count signals, individually at least one quantity of coincidence count signals is counted or transferred and thus a directional information item regarding registered coincidences is available.

In this embodiment variant of the method, as illustrated in FIG. 5, based upon a first matrix-like pixel grid G1 defined by the arrangement of the multiplicity of pixel elements 50 in the X-ray detector 1, as illustrated on the left side, a subpixel grid G2 of subpixels 55 overlapping with the pixel elements 50 of the multiplicity of pixel elements 50 is defined, as illustrated on the right side in FIG. 5. In the example shown, nine original pixel elements 50 of the multiplicity of pixel elements 50 are represented as an example extract with indices 1 to 9, creating the pixel grid G1. The nine pixel elements 50 are formed by a central pixel element 50 of the multiplicity of pixel elements 50 and its four directly adjacent and its four diagonally adjacent pixel elements 50.

The subpixel grid G2 has a reduced grid spacing R2 at least along a grid dimension relative to the pixel grid G1. In the drawing, the first pixel grid G1 has, for example, a first grid spacing R1 horizontally and the subpixel grid G2 has a grid spacing R2 reduced relative thereto. As shown here, the subpixels can, but do not have to, have a square and regular pixel area. Similarly, the grid spacing R2 and/or the pixel area of the subpixel grid G2 can vary locally within the subpixel grid G2.

The subpixels 55 of the subpixel grid G1 overlap with the original pixel elements 50 in the pixel grid G2. The subpixel grid G2 can be defined as in this example such that, at least partially, individual subpixels 55 overlap with at least two original pixel elements 50. In the example shown, for example, the subpixels with the indices b, d, h, f each overlap two pixel elements 50 in the pixel grid G1, the subpixels with the indices a, c, g, i each overlap four original pixel elements 50 in the pixel grid G1 and the subpixel with the index e overlaps only one original pixel element 50 in the pixel grid G1.

In a further step of this embodiment variant of the method for generating an X-ray image dataset, at least one virtual quantity Z of count signals is assigned to each subpixel 55 of the subpixel grid G2. The respective at least one virtual quantity Z of coincidence count signals is thereby based, for at least one portion of the subpixels 55, upon at least one counted or transferred quantity C of coincidence count signals of a pixel element 50 overlapping with the respective subpixel 55. In particular, the virtual quantity Z of count signals assigned to one respective subpixel 55 can be dependent upon the relative position of the virtual subpixel 55 to at least one overlapping, original pixel element 50 of the multiplicity of pixel elements 50.

Subsequently, the X-ray image dataset is generated based upon the virtual quantity Z of count signals assigned to the virtual subpixels 5 in each case.

For example, the at least one virtual quantity Z of count signals which is assigned to a subpixel 55 with the index q can be calculated dependent upon an energy threshold $S \rightarrow S_j$, for example on a weighted sum of the quantities T of count signals and/or the quantities C of coincidence count signals of the respectively overlapping original pixel elements in the original pixel grid G1. A formula for calculating the virtual quantities Z of count signals to be assigned for a subpixel 55 with the index q in respect of the energy threshold $S \rightarrow S_j$ can be provided, for example, as follows:

$$Z_j^q = \sum_p \left( \sum_i a_{ip} T_i^p + \sum_{k,n,m} b_{knmp}{}^p C_{nm}^k \right)$$

where $Z_j^q$ defines the virtual quantity Z in the subpixel 55 with the index q which can be assigned to the energy threshold $S \rightarrow S_j$. $T_i^p$ defines the respectively scanned quantity T of count signals dependent upon the energy threshold $S \rightarrow S_i$ of the original pixel element 50 with the index p. $a_{ip}$ and $b_{knmp}$ define weighting factors. ${}^p C_{nm}{}^k$ defines the respective quantity $C \rightarrow {}^p C_{nm}{}^k$ of coincidence count signals of the original pixel element 50 with the index p in the energy threshold $S \rightarrow S_n$ with the respective further pixel element 50 with the index k in its energy threshold $S \rightarrow S_m$.

Transferred via a coincidence matrix $\hat{C}$ to the representation of the coincidence information, ${}^p C_{nm}{}^k$ corresponds to the entries of the coincidence matrix $\hat{C}$ of the pixel element 50 with the index p with the linked further pixel element 50 having the index k and dependent upon the respectively involved energy thresholds S of the pixel element 50 with the index p and of the linked further pixel element 50 with the index k. The quantity $T \rightarrow T_i^p$ entered here can thereby correspond to an already preprocessed quantity T, e.g. after a linearization.

For illustration, a specific example is described below making use of the pixel grid G1 and the subpixel grid G1 according to FIG. 5. For better intelligibility and to emphasize its significance as a relative specification regarding the pixel element 50 just being considered with the index p, the type of coincidence k, i.e. substantially the further linked pixel element k upon which the coincidence count signals are based is stipulated with a relative geographical specification. This means an index N for "north", an index NE for "northeast", an index E for "east", etc. Proceeding from the pixel element 50 with the index 5 in FIG. 5, the index N would correspond to the pixel element with the index 2, the index E to the index 6, the index NE to the index, etc.

For the specific example, an X-ray detector 1 with a multiplicity of pixel elements 50 is assumed here, each having two comparators 19, each with an energy threshold S. It is further assumed that the coincidence information is available, representable by a completely filled 2×2×8 coincidence matrix $\hat{C}$ for each pixel element 50 of the multiplicity of pixel elements 50 with its directly adjacent and diagonally adjacent pixel elements 50.

The contribution of the central pixel element 50 with the index 5 in FIG. 5 to the virtual quantities Z of the subpixels 55 with the indices a-i in FIG. 5 can, for example, be calculated as follows:

$$Z_1^a = \frac{1}{2} C_{11}^{NW}, \quad Z_2^a = \frac{1}{2}(C_{21}^{NW} + C_{12}^{NW} - C_{22}^{NW})$$

$$Z_1^b = \frac{1}{2} C_{11}^{N}, \quad Z_2^b = \frac{1}{2}(C_{21}^{N} + C_{12}^{N} - C_{22}^{N})$$

$$Z_1^c = \frac{1}{2} C_{11}^{NE}, \quad Z_2^c = \frac{1}{2}(C_{21}^{NE} + C_{12}^{NE} - C_{22}^{NE})$$

$$Z_1^d = \frac{1}{2} C_{11}^{W}, \quad Z_2^d = \frac{1}{2}(C_{21}^{W} + C_{12}^{W} - C_{22}^{W})$$

$$Z_1^f = \frac{1}{2} C_{11}^{E}, \quad Z_2^f = \frac{1}{2}(C_{21}^{E} + C_{12}^{E} - C_{22}^{E})$$

$$Z_1^g = \frac{1}{2} C_{11}^{SW}, \quad Z_2^g = \frac{1}{2}(C_{21}^{SW} + C_{12}^{SW} - C_{22}^{SW})$$

$$Z_1^h = \frac{1}{2} C_{11}^{S}, \quad Z_2^h = \frac{1}{2}(C_{21}^{S} + C_{12}^{S} - C_{22}^{S})$$

$$Z_1^i = \frac{1}{2} C_{11}^{SE}, \quad Z_2^i = \frac{1}{2}(C_{21}^{SE} + C_{12}^{SE} - C_{22}^{SE})$$

$$Z_1^e = T_1^5 - \sum_{k \in NW,N,NE,W,E,SW,S,SE} C_{11}^k,$$

$$Z_2^e = T_2^5 - \sum_{k \in NW,N,NE,W,E,SW,S,SE} (C_{12}^k + C_{21}^k - C_{22}^k)$$

This calculation is carried out for each of the original pixel elements 50 of the multiplicity of pixel elements 50 and the virtual quantities Z obtained are added to any already existing virtual quantity Z in the subpixels. The factor ½ for all the subpixels 55 with indices a to i, except for the subpixel 55 with the index e, corrects the situation that all coincidences are counted in two pixel elements 50 of the pixel grid G1 and therefore, on a transfer of the quantities to the subpixels, would otherwise be counted twice.

From a calculation of this type, it follows that all photons which meet the pixel element with the index 5 centrally in the pixel grid G1 (and thus with a high probability generate no coincidental signals in further pixel elements 50), are counted accordingly in the subpixel 55 with the index e, and all the coincidence events in that subpixel 55 which lies between the two involved original pixel elements 50.

Figure 6:
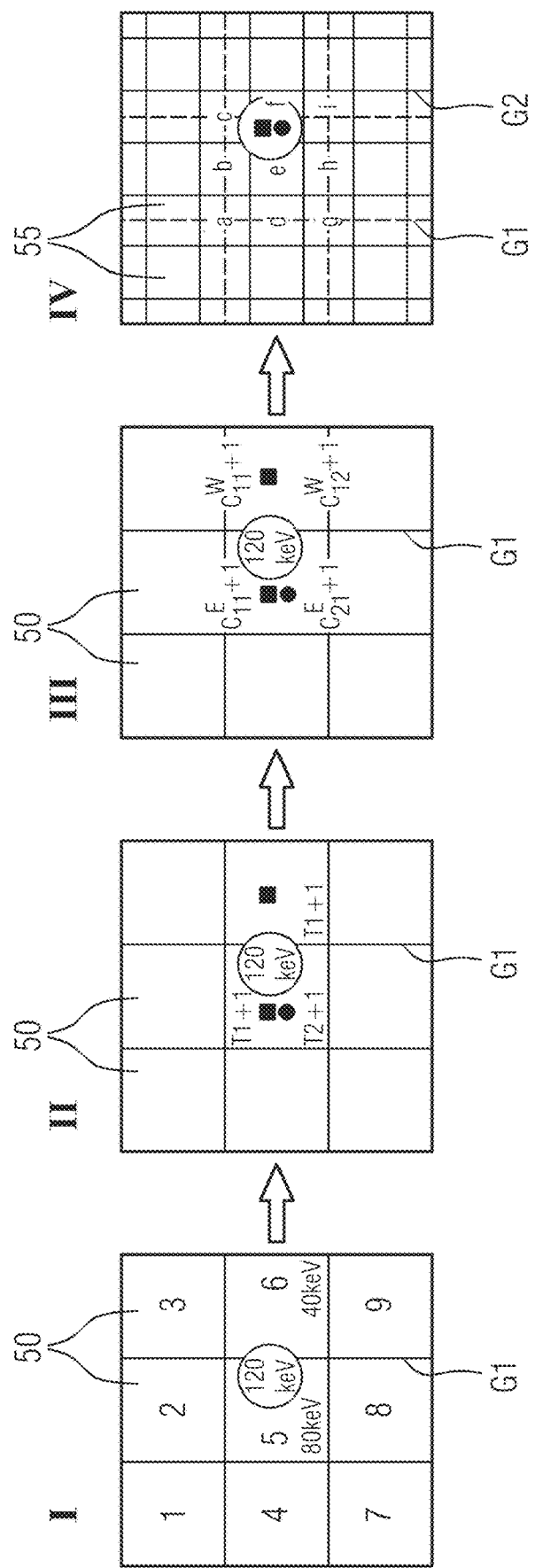
FIG. 6 shows an illustration of the effect of the method for generating an X-ray image dataset on an energy deposition by X-ray radiation within a pixel grid provided by the pixel elements on introduction of a subpixel grid.

The effect of the method described above on the spatial resolution can be illustrated using FIG. 6. If, for example, a 120 keV photon meets the pixel element 50 with the index 5 in FIG. 6 on its right edge (as shown in subview I on the left), the charge generated in the converter element 3 can be divided between the pixel elements 50 with the index 5 and the index 6. In the example shown in FIG. 6, by way of example, 80 keV is deposited in the pixel element with the index 5 and 40 keV in the pixel element with the index 6. In the example shown, in subview II of FIG. 6, this results respectively in a count signal dependent upon the energy threshold S→S$_1$ of the pixel elements with the indices 5 and 6, and in a count signal dependent upon the energy threshold S→S$_2$ of the pixel element with the index 5. The energy threshold S→S$_1$ thereby has, for example, an energy threshold value of 30 keV and the energy threshold S→S$_2$ has an energy threshold value of 60 keV. This means that the quantity T→T$_1$ of count signals based upon the energy threshold S→S$_1$ increases in the pixel element with the index 5 and in the pixel element with the index 6 by one each, the quantity T→T$_2$ based upon the energy threshold S→S$_2$ additionally increases in the pixel element with the index 5 also by one count unit (respectively indicated in the drawing by T$_1$+1 and T$_2$+1). For greater clarity, in the subsequent sub-views III and IV of FIG. 6, the increase of the quantity T→T$_1$ is visualized by the drawn-in square and the increase of the quantity T→T$_2$ is visualized by the drawn-in circle.

At the same time, the X-ray photon generates coincidence count signals in the pixel elements with the indices 5 and 6. The event has the result, in particular, that in the pixel element with the index 5, both the quantity C→C$_{11}^E$ and also the quantity C→C$_{21}^E$ of coincidence count signals is increased by one count unit and in the pixel element with the index 6, correspondingly, both the quantity C→C$_{11}^W$ and also the quantity C→C$_{12}^W$ of coincidence count signals is increased by one count unit (indicated in the drawing by C$_{nm}^E$+1 and C$_{nm}^W$+1.

After the transition to the subpixel grid G2 in subview IV in FIG. 6 and the calculation of the assigned virtual quantities Z of count signals according to the formulae set out above, in the new subpixel with the index f, there results only a single count signal in each of the energy thresholds S→S$_1$ and S→S$_2$. This corresponds to an improved localization of the original location of the incident X-ray photon.

For illustration of the fundamental functioning of the method variant for generating an X-ray image dataset, the example in FIG. 6 has been reduced to a single X-ray photon. However, the method does not operate event-wise, but rather subsequently upon the recorded coincidence information, which corresponds to an integral or a sum of the signals formed via an exposure time window or a readout window. The position of an object relative to the pixel grid is revealed thereby, in particular, as a pattern in the frequencies of the coincidence count signals. In the finer subpixel grid, this additional information can be made useful as a higher resolution. Advantageously, an improved spatial resolution in the X-ray image dataset can be achieved.

For simplification, triple and higher coincidences have been ignored, which, however, can be integrated into the concept in a simple manner. Similarly, such a calculation can also be transferred to other embodiment variants, for example, differently configured subpixel grids and/or a different quantity of energy thresholds and/or a different quantity of respectively linked further pixel elements.

Apart from the regular subpixel grids G2 shown in FIGS. 5 and 6, other variants of the subpixel grid G2 are also possible. A regular subpixel grid represents a particularly suitable and simple variant of the method, which can also make use of common, routinely used image reconstruction and image processing algorithms in a simple manner.

However, differently formed grids can also exist. For example, a finer sampling takes place in just one grid dimension, for example, a subdivision of the original pixel elements 50. For example, the grid spacings of the subpixel grid vary along at least one grid dimension. The defined subpixel grid can be based, in particular, upon the available coincidence information in the pixel elements of the multiplicity of pixel elements. If, for example, coincidence information is gathered between the pixel elements only in the direction of one grid dimension, then a finer subpixel grid can particularly advantageously be implemented along this dimension. If coincidence information is not available for each pixel element of the multiplicity of pixel elements, then in these pixel elements, a subdivision or a finer subpixel grid can be locally dispensed with.

It can further be advantageous, for example, to use the further additional coincidence information from a plurality of energy thresholds S in order to enable a further improved localization of the origin of coincidentally occurring signals. For this purpose, it can be provided in the method, based upon the pixel grid G1, to define a subpixel grid G2 which, as illustrated by way of example in FIG. 7, can also localize coincidences, in which in the pixel element a higher energy threshold S has been triggered than in the respective adjacent pixel element, closer to the pixel center 56 of the pixel element 50 under consideration.

Figure 7:
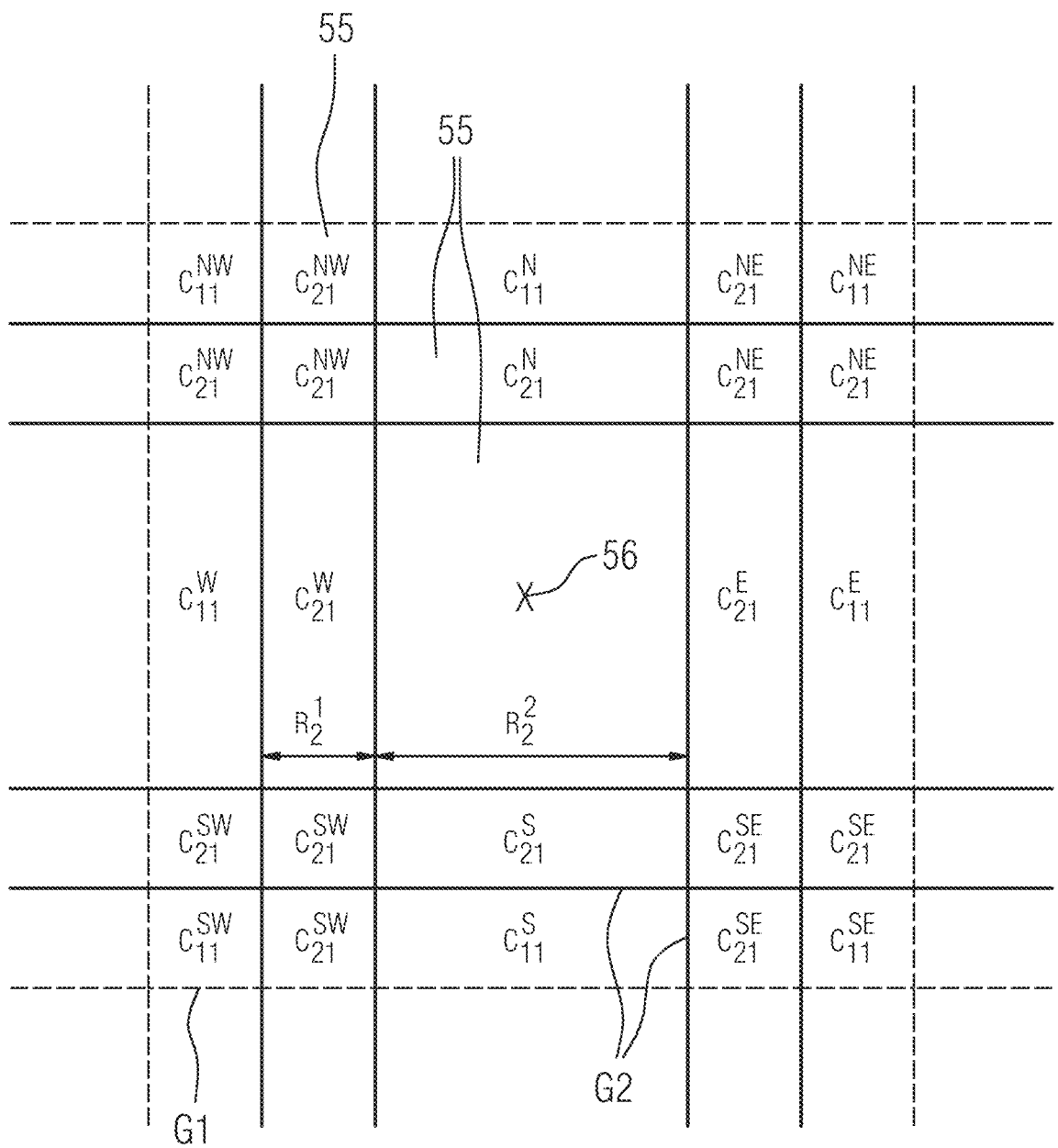
FIG. 7 shows an illustration of a subpixel grid defined on the basis of the pixel grid of pixel elements in a further embodiment.

In FIG. 7, an example subpixel grid G2 is shown which subdivides the pixel grid G1 into a finer grid and wherein the additional coincidence information from a plurality of energy thresholds S is used to achieve a further improved localization of the coincidentally occurring signals. Other embodiment variants of the subpixel grid distinct from the variants shown are also possible. The subpixel grid G1 shown in FIG. 7 by way of example has a non-equidistant sampling, i.e. it has varying grid spacings. In particular, in contrast to the subpixels 55 in FIGS. 5 and 6, the subpixels 55 defined by the subpixel grid G2 shown in FIG. 7 have different areas.

In FIG. 7, the contribution of the respective counted quantities of coincidence count signals to the virtual quantities of count signals in the subpixels 55 for the example subpixel grid G2 is made clear. The quantities $C \rightarrow C_{nm}^{k}$ of coincidence count signals thereby contribute, dependent upon the relative position and, in particular, dependent upon the spacing of the virtual subpixel 55 from the center 56 of the pixel element 50 overlapping in the pixel grid G1 defined by the pixel elements 50. In the example shown in FIG. 7, for example, coincidence count signals which contribute to a quantity $C \rightarrow C_{21}^{k}$ are located closer to the pixel center 56 than coincidence count signals which contribute to a quantity $C \rightarrow C_{11}^{k}$. The counted quantity T of count signals of the overlapping pixel element 50 defined by the pixel grid G1 is assigned to the central subpixel 55, wherein accordingly, the quantities C of coincidence count signals are subtracted. In the example of FIG. 6 above, the index k denotes the type of the coincidence k, i.e. substantially the further linked pixel element k upon which the coincidence count signals are based, in the form of the relative geographical specification.

Underlying this variant is the assumption that the quantities C of coincidence count signals with an (energy-) symmetrical exceeding of energy thresholds in the pixel element 50 under consideration and the adjacent pixel element contain, with a higher probability, events that through an interaction close to the boundary and, associated therewith, the more even distribution of the deposited energy to a plurality of pixel elements have each, with a higher probability, exceeded only the first energy threshold. However, an (energy-)asymmetrical coincidence indicates a larger overlap of the deposited energy with one of the participating original pixel elements and therewith possibly an interaction point further removed from the pixel edge.

It can also be advantageous, in general, in the selection of the subpixel sizes of the subpixel grid G2, to select the pixel size, i.e. the pixel area of the subpixels 55, dependent upon at least one physical parameter which is connected to the charge distribution of the incident X-ray radiation in the converter element 3. A physical parameter can comprise, for example, the expected diameter of the charge distribution generated in the converter element by the absorption of an X-ray photon. It can comprise the expected mean range of fluorescences generated in the sensor material by the absorption of an X-ray photon. Thereby, for example, the energy distribution of the incident X-ray radiation can be taken into account. By this means, a more even ratio of statistics/pixel area and thus a uniform signal-to-noise ratio can advantageously be achieved. This can advantageously lead to a more even image impression.

Figure 8:
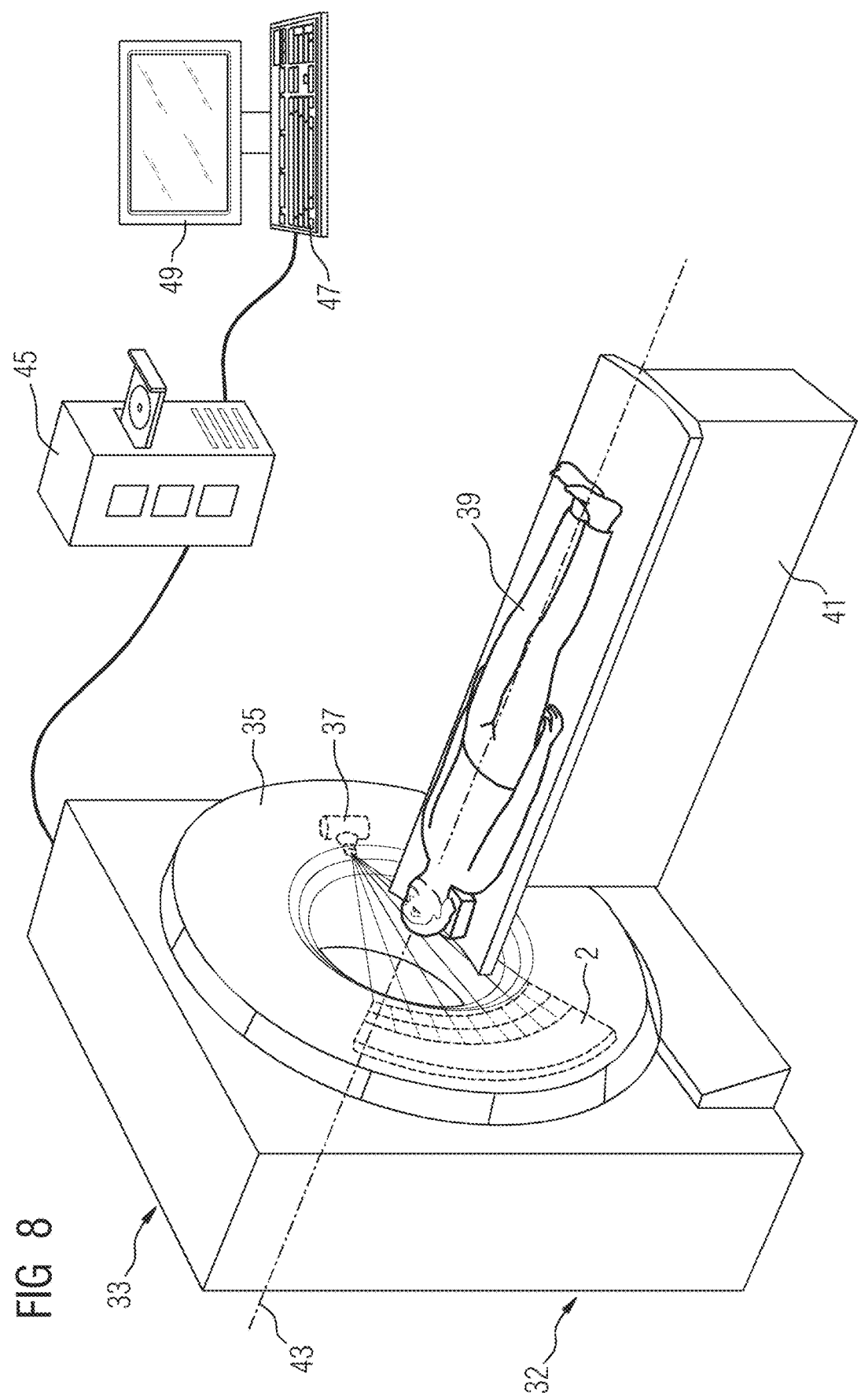
FIG. 8 shows a medical imaging device.

FIG. 8 shows an example embodiment of a medical imaging device 32 according to the invention in the form of a computed tomography system. The computed tomography system 32 comprises a gantry 33 with a rotor 35. The rotor 35 comprises a radiation source or an X-ray source 37 and a detector apparatus 2. The detector apparatus 2 has at least one X-ray detector 1. The detector apparatus 2 can have, in particular, an X-ray detector system 51 according to the invention comprising at least one X-ray detector 1 and a generating unit 71. The X-ray detector system 51, however, can also be distributed at physically different locations of the medical imaging device 32. For example, the X-ray detector or detectors 1 of an X-ray detector system 51 can be included by the detection apparatus 2 and arranged on the rotor and the generating unit 71 can be physically separated therefrom, but connected in a signal-carrying manner, for example, in a static part of the medical imaging device 32. For control of the imaging device 32, a computer unit 45 is used. For example, the generating unit 71 of the X-ray detector system 51 according to the invention can also be included by the computer unit 45. An input unit 47 and an output unit 49 are connected to the computer unit 45. An input unit 47 and/or output unit 49 enables, for example, the manual interaction of a user, for example, the starting or stopping of the method according to the invention.

The generating unit 71 and/or the computer unit 45 can be implemented in the form of a computer, a microcontroller or an integrated circuit. The generating unit 71 and/or the computer unit 45 can have hardware elements or software elements, for example, a microprocessor or a so-called FPGA (Field Programmable Gate Array). It can also be a real or virtual grouping of computers (a specialist term for a real grouping being a "cluster" and for a virtual grouping, a "cloud").

The examination object 39, in this case the patient, is positioned on the patient support 41 and is movable along the rotation axis z 43 through the gantry 33. The object can also be, for example, an animal examination object.

For the recording of an X-ray image dataset, typically, the detection apparatus 2 comprising the X-ray detector 1 and the X-ray source 37 rotates about the rotation axis z, wherein scan data is recorded from different angular regions via the X-ray detector 1 based upon the X-ray radiation passing through the object 39. Based upon the possibly preprocessed scan data, via a reconstruction algorithm, for example, a filtered back projection or an iterative reconstruction algorithm, three-dimensional volume image data can be generated. Proceeding from this three-dimensional volume image data, two dimensional slice images, which each represent a sectional image through the imaged volume, can be generated.

In the context of the invention, the scan data can comprise the quantities T of count signals and the quantities C of coincidence count signals ascertained in the pixel elements 50 of the multiplicity of pixel elements 50 or the subset of the multiplicity of pixel elements 50, wherein the quantities C of coincidence count signals can enter a preprocessing of the scan data for the generation of the image dataset, the image reconstruction itself and/or also into a postprocessing of a reconstructed preliminary image dataset.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating an X-ray image dataset via a photon-counting X-ray detector, the photon-counting X-ray detector including a converter and a multiplicity of pixel elements, the converter being configured to convert X-ray radiation into an electrical signal, the multiplicity of pixel elements including first pixel elements, and at least a subset of the multiplicity of pixel elements including second pixel elements, the method comprising:

first counting at least one quantity of count signals in a respective first pixel element among the first pixel elements based on X-ray radiation incident on the multiplicity of pixel elements, each count signal among the at least one quantity of count signals being based on a corresponding electrical signal from the converter directly entering the respective first pixel element;

second counting at least one quantity of coincidence count signals in a respective second pixel element among the second pixel elements, a respective coincidence count signal among the at least one quantity of coincidence count signals being based on coincidently occurring electrical signals from the converter directly entering both the respective first pixel element and the respective second pixel element, the at least one quantity of coincidence count signals being counted based on a first output signal of at least one first comparator and a second output signal of at least one second comparator, the at least one first comparator being included in the respective first pixel element, and the at least one second comparator being included in the respective second pixel element; and generating an X-ray image dataset based on the at least one quantity of count signals and the at least one quantity of coincidence count signals.

2. The method of claim 1, wherein the generating the X-ray image dataset comprises:
performing data preprocessing before performing first image reconstruction, the data preprocessing being based on the at least one quantity of coincidence count signals;
performing second image reconstruction based on the at least one quantity of coincidence count signals; or
performing postprocessing downstream of performing third image reconstruction, the postprocessing being based on the at least one quantity of coincidence count signals.

3. The method of claim 2, further comprising:
adapting the at least one quantity of count signals in at least each individual second pixel element among the second pixel elements based on the at least one quantity of coincidence count signals counted in the individual second pixel element.

4. The method of claim 2, wherein the generating the X-ray image dataset comprises:
generating a preliminary image dataset based on the at least one quantity of count signals;
generating a coincidence image dataset based on the at least one quantity of coincidence count signals; and
applying the coincidence image dataset to the preliminary image dataset.

5. The method of claim 2, wherein the generating the X-ray image dataset comprises using a trained function, the at least one quantity of coincidence count signals being an input parameter of the trained function.

6. The method of claim 2, wherein
each respective pixel element among the multiplicity of pixel elements includes a quantity of comparators among a plurality of comparators, each respective comparator among the plurality of comparators including an adjustable energy threshold, the plurality of comparators including the at least one first comparator and the at least one second comparator;
the first counting counts the at least one quantity of count signals based on the first output signal of the at least one first comparator; and
the second counting counts the at least one quantity of coincidence count signals based on the first output signal and the second output signal of the at least one second comparator.

7. The method of claim 2, wherein the respective second pixel element is directly adjacent or diagonally adjacent to the respective first pixel element.

8. The method of claim 1, further comprising:
adapting the at least one quantity of count signals in at least each individual second pixel element among the second pixel elements based on the at least one quantity of coincidence count signals counted in the individual second pixel element.

9. The method of claim 1, wherein the generating the X-ray image dataset comprises:
generating a preliminary image dataset based on the at least one quantity of count signals;

generating a coincidence image dataset based on the at least one quantity of coincidence count signals; and applying the coincidence image dataset to the preliminary image dataset.

10. The method of claim 1, wherein the generating the X-ray image dataset comprises using a trained function, the at least one quantity of coincidence count signals being an input parameter of the trained function.

11. The method of claim 1, wherein
each respective pixel element among the multiplicity of pixel elements includes a quantity of comparators among a plurality of comparators, each respective comparator among the plurality of comparators including an adjustable energy threshold, the plurality of comparators including the at least one first comparator and the at least one second comparator;

the first counting counts the at least one quantity of count signals based on the first output signal of the at least one first comparator; and the second counting counts the at least one quantity of coincidence count signals based on the first output signal and the second output signal of the at least one second comparator.

12. The method of claim 11, wherein the adjustable energy threshold of the at least one first comparator and the adjustable energy threshold of the at least one second comparator have a same energy threshold value.

13. The method as claimed in claim 11, wherein the adjustable energy threshold of the at least one first comparator and the adjustable energy threshold of the at least one second comparator have different energy threshold values.

14. The method of claim 11, wherein
each of the second pixel elements includes two or more comparators; and the at least one quantity of coincidence count signals includes a plurality of quantities of coincidence count signals, each quantity of coincidence count signals among the plurality of quantities of coincidence count signals being based on a corresponding output signal from a respective comparator among the two or more comparators of the respective second pixel element.

15. The method of claim 11, wherein the respective second pixel element is directly adjacent diagonally adjacent to the respective first pixel element.

16. The method of claim 1, wherein the respective second pixel element is directly adjacent or diagonally adjacent to the respective first pixel element.

17. The method of claim 1, further comprising:
generating coincidence count signals in each of the second pixel elements with respect to between one and 24 first pixel elements, wherein the second counting counts a single quantity of coincidence count signals for all the first pixel elements.

18. The method of claim 1, further comprising:
generating coincidence count signals in each of the second pixel elements with respect to between one and 24 first pixel elements, wherein the second counting counts a separate quantity of coincidence count signals for each of the first pixel elements.

19. The method of claim 18, wherein
the multiplicity of pixel elements form a pixel grid, a subpixel grid of subpixels overlaps the multiplicity of pixel elements, the subpixel grid having a reduced spacing in at least one grid dimension relative to the pixel grid;

the method further comprises assigning at least one virtual quantity of count signals to each respective subpixel among the subpixels based on a counted or transferred quantity of coincidence count signals of a pixel element overlapping the respective subpixel; and the generating the X-ray image dataset generates the X-ray image dataset based on the at least one virtual quantity of count signals.

20. The method of claim 19, wherein the at least one virtual quantity of count signals is based on a spacing of the respective subpixel from a center of the pixel element overlapping the respective subpixel.

21. The method of claim 19, wherein an area differs among the subpixels.

22. The method of claim 1, further comprising:
transferring the at least one quantity of coincidence count signals to the first respective pixel element to obtain at least one transferred quantity of coincidence count signals, and wherein the generating the X-ray image dataset is based on the at least one transferred quantity of coincidence count signals.

23. The method of claim 1, further comprising:
ascertaining a respective quantity of coincidence count signals for each of the multiplicity of pixel elements based on,
the second counting, or
a transferred quantity of coincidence count signals.

24. An X-ray detector system, comprising:
a photon-counting X-ray detector including a converter and a multiplicity of pixel elements, the converter being configured to convert X-ray radiation into an electrical signal, each respective pixel element among the multiplicity of pixel elements being configured to generate a count signal based on a corresponding electrical signal from the converter directly entering the respective pixel element, at least a subset of the multiplicity of pixel elements being configured to generate a coincidence count signal based on a corresponding electrical signal from the converter directly entering both the respective pixel element and at least one other pixel element among the multiplicity of pixel elements; and a generating device configured to generate an X-ray image dataset based on at least one quantity of count signals and at least one quantity of coincidence count signals, the at least one quantity of count signals being counted in each of the multiplicity of pixel elements based on the count signal, and the at least one quantity of coincidence count signals being counted in each pixel element among the subset of the multiplicity of pixel elements based on the coincidence count signal, the at least one quantity of coincidence count signals being counted based on a first output signal of at least one first comparator and a second output signal of at least one second comparator, the at least one first comparator being included in the respective pixel element, and the at least one second comparator being included in the at least one other pixel element.

25. A medical imaging device comprising the X-ray detector system of claim 24.

26. The medical imaging device of claim 25, wherein the medical imaging device is a computed tomography system.

* * * * *